US010435389B2

(12) United States Patent
Volkmann et al.

(10) Patent No.: US 10,435,389 B2
(45) Date of Patent: Oct. 8, 2019

(54) OCTAHYDROCYCLOPENTA[C]PYRROLE ALLOSTERIC INHIBITORS OF SHP2

(71) Applicant: Krouzon Pharmaceuticals, Inc., New Haven, CT (US)

(72) Inventors: Robert Volkmann, Groton, CT (US); Anthony Marfat, Groton, CT (US); Frederick Nelson, Groton, CT (US); Panayiotis Zagouras, Groton, CT (US)

(73) Assignee: Krouzon Pharmaccuticals, Inc., New Haven, CT (US)

( * ) Notice: Subject to any disclaimer, the term of this patent is extended or adjusted under 35 U.S.C. 154(b) by 0 days.

(21) Appl. No.: 16/127,772

(22) Filed: Sep. 11, 2018

(65) Prior Publication Data

US 2019/0077792 A1    Mar. 14, 2019

Related U.S. Application Data

(60) Provisional application No. 62/556,713, filed on Sep. 11, 2017.

(51) Int. Cl.
*C07D 261/10* (2006.01)
*C07D 401/14* (2006.01)
*C07D 413/14* (2006.01)
*C07D 403/04* (2006.01)
*A61P 35/00* (2006.01)

(52) U.S. Cl.
CPC ............ *C07D 403/04* (2013.01); *A61P 35/00* (2018.01); *C07D 401/14* (2013.01)

(58) Field of Classification Search
CPC ... C07D 261/10; C07D 401/14; C07D 413/14
See application file for complete search history.

(56) References Cited

U.S. PATENT DOCUMENTS

| 4,169,846 | A |  | 10/1979 | Kidani et al. |  |
|---|---|---|---|---|---|
| 4,261,989 | A |  | 4/1981 | Sasaki et al. |  |
| 5,266,573 | A |  | 11/1993 | Croci et al. |  |
| 5,621,002 | A |  | 4/1997 | Bosslet et al. |  |
| 6,106,864 | A |  | 8/2000 | Dolan et al. |  |
| 6,780,996 | B2 |  | 8/2004 | Boschelli et al. |  |
| 8,865,738 | B2 | * | 10/2014 | Abouabdellah | C07D 231/12 514/312 |
| 2015/0080362 | A1 | * | 3/2015 | Branstrom | A01N 43/40 514/210.2 |
| 2017/0204080 | A1 |  | 7/2017 | Chen et al. |  |

FOREIGN PATENT DOCUMENTS

| CN | 107286150 | 10/2017 |
|---|---|---|
| WO | WO 91/11172 | 8/1991 |
| WO | WO 94/02518 | 2/1994 |
| WO | WO 98/55148 | 12/1998 |
| WO | WO 99/63984 | 12/1999 |
| WO | WO 00/35298 | 6/2000 |
| WO | WO 2001/002369 | 1/2001 |
| WO | WO 2002/010192 | 2/2002 |
| WO | WO 2002/066470 | 8/2002 |
| WO | WO 2003/064383 | 8/2003 |
| WO | WO 2003/075836 | 9/2003 |
| WO | WO 2005/028443 | 3/2004 |
| WO | WO 2006/122806 | 11/2006 |
| WO | WO 2009/036082 | 3/2009 |
| WO | WO 2009/055730 | 4/2009 |
| WO | WO 2009/155386 | 12/2009 |
| WO | WO 2013/033240 | 3/2013 |
| WO | WO 2015/107493 | 7/2015 |
| WO | WO 2015/107494 | 7/2015 |
| WO | WO 2015/107495 | 7/2015 |
| WO | WO 2016/203404 | 12/2016 |
| WO | WO 2016/203405 | 12/2016 |
| WO | WO 2016/203406 | 12/2016 |
| WO | WO 2017/156397 | 9/2017 |
| WO | WO 2017/211303 | 12/2017 |
| WO | WO 2017/216706 | 12/2017 |
| WO | WO 2018/013597 | 1/2018 |
| WO | WO 2018/057884 | 3/2018 |
| WO | WO 2018/081091 | 5/2018 |
| WO | WO 2018/130928 | 7/2018 |
| WO | WO 2018/136264 | 7/2018 |
| WO | WO 2018/136265 | 7/2018 |
| WO | WO 2018/218133 | 11/2018 |

OTHER PUBLICATIONS

Bhatarai et al. (Chemical & Pharmaceutical Bulletin (2014), 62(12), 1214-1224).*
Almarsson and Zaworotko, "Crystal engineering of the composition of pharmaceutical phases. Do pharmaceutical co-crystals represent a new path to improved medicines?" Chem Commun., Sep. 2004, 17:1889-1896.
Bagdanoff et al., "Optimization of Fused Bycyclic Allosteric SHP2 Inhibitors," J Med Chem., 2019, 62:1781-1792.
Batth et al., "Large-Scale Phosphoproteomics Reveals Shp-2 Phosphatase-Dependent Regulators of Pdgf Receptor Signaling," Cell Rep., Mar. 6, 2018, 22(10):2784-2796.
Chen et al., "Allosteric Inhibition of SHP2 phosphatase inhibits cancers driven by receptor tyrosine kinases," Nature, Jul. 7, 2016, 535(7610):148-152.
Cho et al., "Synthesis and biological evaluation of azobicyclo[3.3.0] octane derivatives as dipeptidyl peptidase 4 inhibitors for the treatment of type 2 diabetes," Bioorg Med Chem Lett, Jun. 15, 2010, 20(12):3565-3568.
Clare et al., "Voltage-gated sodium channels as therapeutic targets," Therapeutic Focus, Nov. 11, 2000, 5(11):506-520.
Dardaei et al., "SHP2 inhibition restores sensitivity in ALK-rearranged non-small-cell lung cancer resistant to ALK inhibitors," Nat Med., May 2018, 24(4):512-517.
Finnin and Morgan, "Transdermal penetration enhancers: applications, limitations, and potential," J Pharm Sci, Oct. 1999, 88(10):955-958.

(Continued)

*Primary Examiner* — Bruck Kifle
(74) *Attorney, Agent, or Firm* — Fish & Richardson P.C.

(57) ABSTRACT

The present invention relates to compounds capable of inhibiting the activity of SHP2. The invention further provides a process for the preparation of compounds of the invention, pharmaceutical preparations comprising such compounds, and methods of using such compounds and compositions in the management of diseases or disorders associated with the aberrant activity of SHP2.

20 Claims, No Drawings

(56) References Cited

OTHER PUBLICATIONS

Flemming, "Cancer: Allosteric phosphatase inhibitor puts brake on cancer cells," Nat Rev Drug Discov., 2016, 15(8):530-531.
Fortanet et al., "Allosteric Inhibition of SHP2: Identification of a Potent, Selective, and Orally Efficacious Phosphatase Inhibitor," J Med Chem., Sep. 8, 2016, 59(17):7773-7782.
Haleblian, "Characterization of habits and crystalline modification of solids and their pharmaceutical applications," J Pharm Sci, Aug. 1975, 64(8):1269-1288.
International Search Report and Written Opinion in International Application No. PCT/US2018/050397, dated Jan. 3, 2019, 20 pages.
Invitation to Pay Fees in International Application No. PCT/US2018/050397, dated Nov. 13, 2018, 15 pages.
Jin et al., "Scaffold-based novel SHP2 allosteric inhibitors design using Receptor-Ligand pharmacophore model, virtual screening and molecular dynamics," Comput Biol Chem., Apr. 2018, 73:179-188.
Kostallari et al., "Hepatic stellate cell-derived platelet-derived growth factor receptor-alpha-enriched extracellular vesicles promote liver fibrosis in mice through SHP2," Hepatology, Jul. 2018, 68(1):333-348.
Kulton et al., "Abstract 4878: Discovery of an allosteric inhibitor of SHP2, RMC-4550," Poster, Presented at Proceedings of the AACR Annual Meeting 2018, Chicago IL, Apr. 14-18, 2018, Jul. 2018, 78(13): 3 pages.
LaRochelle et al., "Structural reorganization of SHP2 by oncogenic mutations and implications for oncoprotein resistance to allosteric inhibition," Nat Commun., Oct. 30, 2018, 9(1):4508.
Liang and Chen, "Fast-dissolving intraoral drug delivery systems," Expert Opinion in Therapeutic Patents, 2001, 11(6):981-986.
Nichols et al., "RAS nucleotide cycling underlies the SHP2 phosphatase dependence of mutant BRAF-, NF1- and RAS-driven cancers," Nat Cell Biol., Sep. 2018, 20(9):1064-1073.
Padua et al., "Mechanism of activating mutations and allosteric drug inhibition of the phosphatase SHP2," Nat Commun., Oct. 30, 2018, 9(1):4507.
Sun et al., "Selective inhibition of leukemia-associated SHP2E69K mutant by the allosteric SHP2 inhibitor SHP099," Leukemia, May 2018, 32(5):1246-1249.
STN Report, dated Aug. 14, 2018, 7 pages.
STN Report, dated Aug. 31, 2018, 21 pages.
Verma et al., "Drug Delivery Technology and Future Directions," Pharmaceutical Technology On-line, 2001, 25(2):1-14.

\* cited by examiner

OCTAHYDROCYCLOPENTA[C]PYRROLE ALLOSTERIC INHIBITORS OF SHP2

CLAIM OF PRIORITY

This application claims priority to U.S. Provisional Patent Application Ser. No. 62/556,713, filed on Sep. 11, 2017, the entire contents of which are hereby incorporated by reference.

FIELD OF THE INVENTION

The present invention relates to compounds capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

BACKGROUND OF THE INVENTION

The Src Homolgy-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, Crouzon Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present invention fulfill the need of small molecules to that inhibit the activity of SHP2.

SUMMARY

The present disclosure provides, inter alia, a compound of Formula A1:

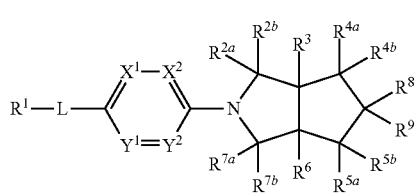

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier.

The present disclosure further provides methods of modulating (e.g., inhibiting) SHP2 activity, which comprises administering to an individual a compound of the disclosure, or a pharmaceutically acceptable salt thereof.

The present disclosure further provides methods of treating or preventing a disease in a patient, comprising administering a therapeutically effective amount of a compound of the invention, or a pharmaceutically acceptable salt thereof, to the patient in need of such treatment or prevention, wherein the disease is mediated by activity of SHP2.

The present disclosure also provides uses of the compounds described herein in the manufacture of a medicament for use in therapy. The present disclosure also provides the compounds described herein for use in therapy.

DETAILED DESCRIPTION

The present invention relates to novel octahydrocyclopenta[c]pyrroles including their pharmaceutically acceptable salts. The invention also relates to processes for the preparation of, intermediates used in the preparation of, pharmaceutical compositions, and the uses of such compounds in treating SHP2 mediated disorders such as cancer.

Compounds

The present disclosure provides an inhibitor of SHP2 which is a compound of Formula A1:

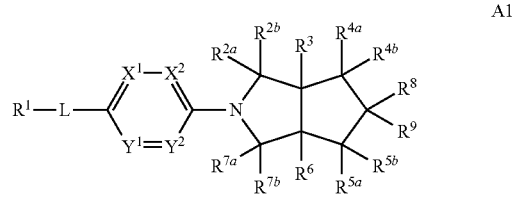

or a pharmaceutically acceptable salt thereof, wherein:
L is O, S, or absent;
$X^1$ is N or $CR^{X1}$;
$X^2$ is N or $CR^{X2}$;
$Y^1$ is N or $CR^{Y1}$;
$Y^2$ is N or $CR^{Y2}$;
wherein not more than 3 of $X^1$, $X^2$, $Y^1$, and $Y^2$ are simultaneously N;
$R^1$ is $C_{6-10}$ aryl, $C_{3-14}$ cycloalkyl, 5-14 membered heteroaryl, or 4-14 membered heterocycloalkyl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, and $C_{2-6}$ alkynyl are optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^{2a}$, $R^{2b}$, $R^{4a}$, $R^{4b}$, $R^{5a}$, $R^{5b}$, $R^{7a}$, and $R^{7b}$ are each independently selected from H, $C_{1-4}$ alkyl, $C_{1-4}$ alkoxy, amino, hydroxy, $C_{3-8}$ cycloalkyl and $C_{1-4}$ alkylamino;

$R^3$ and $R^6$ are each independently selected from H, F, or $C_{1-4}$ alkyl;

$R^8$ and $R^9$ are each independently selected from H, halo, $C_{1-6}$ alkyl, $C_{2-6}$ alkenyl, $C_{2-6}$ alkynyl, $C_{1-4}$ haloalkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)OR^{a2}$ $NR^{c2}C(O)NR^{c2}R^{d2}$ $NR^{c2}S(O)R^{b2}$, $NR^{c2}S(O)_2R^{b2}$ $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the alkyl, $C_{2-6}$ alkenyl, and $C_{2-6}$ alkynyl are optionally substituted with 1, 2, or 3 substituents independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$ $NR^{c2}R^{d2}$, $NR^{c2}C(O)R^{b2}$, $NR^{c2}C(O)OR^{a2}$, $NR^{c2}C(O)NR^{c2}R^{d2}$ $NR^{c2}S(O)R^{b2}$ $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

wherein at least one of $R^8$ and $R^9$ is other than H;

$R^{X1}$, $R^{X2}$, $R^{Y1}$, and $R^{Y2}$ are each independently selected from H, $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein the $C_{1-6}$ alkyl, $C_{2-6}$ alkenyl, and $C_{2-6}$ alkynyl are optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^2$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$ $NR^{c3}C(=NR^{e3})NR^{c3}R^{d3}$ $NR^{c3}R^{d3}$, $NR^{c3}C(O)R^{b3}$, $NR^{c3}C(O)OR^{a3}$, $NR^{c3}C(O)NR^{c3}R^{d3}$ $NR^{c3}S(O)R^{b3}$ $NR^{c3}S(O)_2R^{b3}$, $NR^{c3}S(O)_2NR^{c3}R^{d3}S(O)R^{b3}$, $S(O)NR^{c3}R^{d3}$, $S(O)_2R^{b3}$, and $S(O)_2NR^{c3}R^{d3}$;

each $R^{a1}$, $R^{b1}$, $R^{c1}$, $R^{d1}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^{a1}$, $R^{b1}$, $R^{c1}$, $R^{d1}$, $R^{a3}$, $R^{b3}$, $R^{c3}$, and $R^{d3}$ are each optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c7}R^{d4}$ $NR^{c4}C(O)OR^{a4}$, $C(=NR^{e4})NR^{c4}R^{d4}$, $NR^{c4}C(=NR^{e4})NR^{c3}R^{d4}S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c1}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a4}SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$ $NR^{c4}C(O)NR^{c7}R^{d4}$ $NR^{c4}C(O)OR^{a4}$, $C(=NR^{e4})NR^{c4}R^{d4}$, $NR^{c4}C(=NR^{e4})$ $NR^{c3}R^{d4}S(O)R^{b4}$, $S(O)NR^{c4}R^{d4}$, $S(O)_2R^{b4}$, $NR^{c4}S(O)_2R^{b4}$ $NR^{c4}S(O)_2NR^{c4}R^{d4}$, and $S(O)_2NR^{c4}R^{d4}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$ $NR^{c4}C(O)NR^{c7}R^{d4}$ $NR^{c4}C(O)OR^{a4}$, $C(=NR^{e4})NR^{c4}R^{d4}$, $NR^{c4}C(=NR^{e4})$ $NR^{c3}R^{d4}S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{a2}$, $R^{b2}$, $R^{c2}$, and $R^{d2}$ is independently selected from H and $C_{1-4}$ alkyl;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^{e1}$, $R^{e2}$, $R^3$, and $R^{e4}$ is independently selected from H, $C_{1-4}$ alkyl, and CN, wherein any aforementioned heteroaryl or heterocloalkyl group comprises 1, 2, 3, or 4 ring-forming heteroatoms independently selected from O, N, and S; and wherein one or more ring-forming C or N atoms of any aforementioned heterocycloalkyl group is optionally substituted by an oxo (=O) group.

In some embodiments, L is absent.
In some embodiments, L is O.
In some embodiments, L is S.
In some embodiments, $X^1$ is N.
In some embodiments, $X^1$ is $CR^{X1}$.
In some embodiments, $X^2$ is N.
In some embodiments, $X^2$ $CR^{X2}$.
In some embodiments, $X^1$ is $CR^{X1}$ and $X^2$ is N.

In some embodiments, $Y^1$ is N.
In some embodiments, $Y^1$ is $CR^{Y1}$.
In some embodiments, $Y^2$ is N.
In some embodiments, $Y^2$ is $CR^{Y2}$.
In some embodiments, $X^1$ is $CR^{X1}$, $X^2$ is N, and $Y^2$ is N.
In some embodiments, $X^1$ is $CR^{X1}$, $X^2$ is N, and $Y^1$ is N.
In some embodiments, $X^1$ is $CR^{X1}$, $X^2$ is N, $Y^1$ is N and $Y^2$ is N.

In some embodiments, $R^1$ is $C_{6-10}$ aryl or 5-14 membered heteroaryl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$. In some embodiments, $R^1$ is phenyl or 6-membered heteroaryl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^1$ is phenyl or 6-membered heteroaryl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently substituted with 1, 2, or 3 substituents independently selected from halo, $C_{1-6}$ alkyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^1$ is phenyl optionally substituted with 1, 2, or 3 substituents independently selected from F, Cl, methyl, and $CF_3$.

In some embodiments, $R^1$ is pyridyl optionally substituted with 1, 2, or 3 substituents independently selected from F, Cl, methyl, and $CF_3$.

In some embodiments, $R^1$ is 2-chloro-3-methylphenyl, 2,3-dichlorophenyl, 2-chloro-3-fluorophenyl, 2-chloropyridin-3-yl, 3-chloro-2-fluorophenyl, or 2-chloro-3-(trifluoromethyl)phenyl.

In some embodiments, $R^3$ and $R^6$ are both H.

In some embodiments, $R^{2a}$, $R^{2b}$, $R^{4a}$, $R^{4b}$, $R^{5a}$, $R^{5b}$, $R^{7a}$, and $R^{7b}$ are all H.

In some embodiments, $R^8$ and $R^9$ are each independently selected from H, halo, $C_{1-6}$ alkyl, $C_{1-4}$ haloalkyl, $OR^{a2}$, and $NR^{c2}R^{d2}$, wherein the alkyl is optionally substituted with 1, 2, or 3 substituents independently selected from halo, $OR^{a2}$, and $NR^{c2}R^{d2}$.

In some embodiments, $R^8$ and $R^9$ are each independently selected from H, $C_{1-4}$ alkyl, OH, and $NH_2$, wherein the alkyl is optionally substituted with $NH_2$.

In some embodiments, $R^8$ and $R^9$ are each independently selected from methyl and $NH_2$.

In some embodiments, $R^{X1}$, $R^{X2}$, $R^{Y1}$, and $R^{Y2}$ are each independently selected from H, $C_{1-6}$ alkyl, and $NR^{c3}R^{d3}$, wherein the $C_{1-6}$ alkyl is optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$ $NR^{c3}R^{d3}$, $NR^{c3}C(O)R^{b3}$ $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^{X1}$ is selected from H, $C_{1-6}$ alkyl, and $NR^{c3}R^{d3}$, wherein the $C_{1-6}$ alkyl is optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$ $NR^{c3}R^{d3}$, $NR^{c3}C(O)R^{b3}$, $NR^{c3}C(O)OR^{a3}$, $NR^{c3}C(O)NR^{c3}R^{d3}$ $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^{X1}$ is selected from methyl and $NH_2$.

In some embodiments, $R^{X1}$ is $NH_2$.
In some embodiments, $R^{X2}$ is H.
In some embodiments, $R^{Y1}$ is H.
In some embodiments, $R^{Y2}$ is H.

In some embodiments, the compound of Formula A1 has Formula A2:

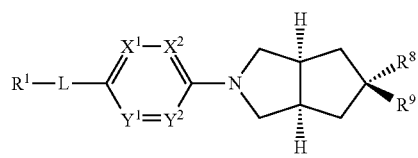

A2 or a pharmaceutically acceptable salt thereof.

In some embodiments, the compound of Formula A1 has Formula A2a or A2b:

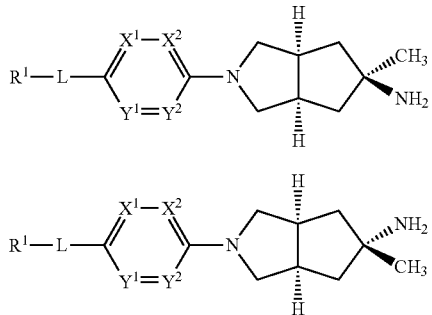

or a pharmaceutically acceptable salt thereof.

In some embodiments, the compound of Formula A1 has Formula A3a, A3b, or A3c:

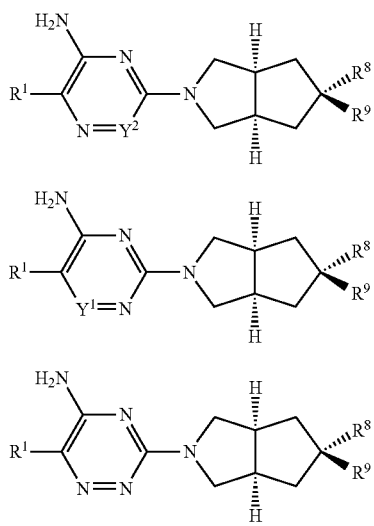

or a pharmaceutically acceptable salt thereof.

In some embodiments, the compound of Formula A1 is selected from:

(3aR,5r,6aS)-2-(6-amino-5-(2-chloro-3-methylphenyl) pyrazin-2-yl)-5-methyloctahydrocyclopenta[c]pyrrol-5-amine;

(3aR,5r,6aS)-2-(6-amino-5-(2,3-dichlorophenyl)pyrazin-2-yl)-5-methyloctahydrocyclopenta[c]pyrrol-5-amine;

(3aR,5r,6aS)-2-(6-amino-5-(2-chloro-3-fluorophenyl) pyrazin-2-yl)-5-methyloctahydrocyclopenta[c]pyrrol-5-amine;

(3aR,5r,6aS)-2-(6-amino-5-(2-chloropyridin-3-yl)pyrazin-2-yl)-5-methyloctahydrocyclopenta[c]pyrrol-5-amine;

(3aR,5r,6aS)-2-(6-amino-5-(3-chloro-2-fluorophenyl) pyrazin-2-yl)-5-methyloctahydrocyclopenta[c]pyrrol-5-amine;

3aR,5r,6aS)-2-(6-amino-5-(2-chloro-3-(trifluoromethyl) phenyl)pyrazin-2-yl)-methyloctahydrocyclopenta[c]pyrrol-5-amine;

(3aR,5s,6aS)-2-(6-amino-5-(2,3-dichlorophenyl)pyrazin-2-yl)-5-methyloctahydrocyclopenta[c]pyrrol-5-amine;

(3aR,5s,6aS)-2-(6-amino-5-(2-chloro-3-methylphenyl) pyrazin-2-yl)-5-methyloctahydrocyclopenta[c]pyrrol-5-amine;

6-((3aR,5r,6aS)-5-(aminomethyl)-5-methylhexahydrocyclopenta[c]pyrrol-(2,3-dichlorophenyl)pyrazin-2-amine;

6-((3aR,5s,6aS)-5-(aminomethyl)-5-methylhexahydrocyclopenta[c]pyrrol-(2,3-dichlorophenyl)pyrazin-2-amine;

(3aR,5r,6aS)-2-(4-amino-5-(2-chloro-3-methylphenyl)pyrimidin-2-yl)-5-methyloctahydrocyclopenta[c]pyrrol-5-amine;

(3aR,5r,6aS)-2-(4-amino-5-(2,3-dichlorophenyl)pyrimidin-2-yl)-5-methyloctahydrocyclopenta[c]pyrrol-5-amine;

(3aR,5r,6aS)-2-(4-amino-5-(2-chloro-3-fluorophenyl)pyrimidin-2-yl)-5-methyloctahydrocyclopenta[c]pyrrol-5-amine; and (3aR,5r,6aS)-2-(4-amino-5-(2-chloropyridin-3-yl)pyrimidin-2-yl)-5-methyloctahydrocyclopenta[c]pyrrol-5-amine;

or a pharmaceutically acceptable salt thereof.

Also provided herein are compounds of Formula B1:

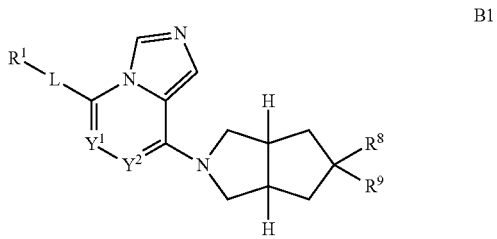

wherein $R^1$, L, $Y^1$, $Y^2$, $R^8$, and $R^9$ are as defined according to any of the embodiments described herein. In some embodiments, one of $R^8$ and $R^9$ is methyl and the other is amino. The compounds of Formula B1 can be prepared in an analogous manner to the synthetic routes presented in the Schemes herein.

Also provided herein are compounds of Formula C1:

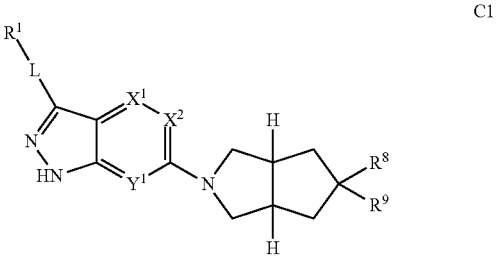

wherein $R^1$, L, $X^1$, $X^2$, $Y^1$, $R^8$, and $R^9$ are as defined according to any of the embodiments described herein. In some embodiments, one of $R^8$ and $R^9$ is methyl and the other is amino. The compounds of Formula C1 can be prepared in an analogous manner to the synthetic routes presented in the Schemes herein.

Also provided herein are compounds of Formula D1:

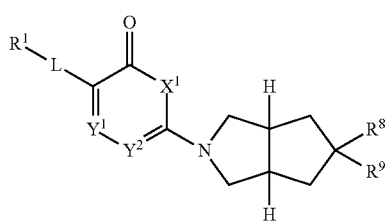

wherein R¹, L, X¹, Y¹, Y², R⁸, and R⁹ are as defined according to any of the embodiments described herein. In some embodiments, one of R⁸ and R⁹ is methyl and the other is amino. The compounds of Formula D1 can be prepared in an analogous manner to the synthetic routes presented in the Schemes herein.

In one aspect, the present invention provides compounds of Formula I:

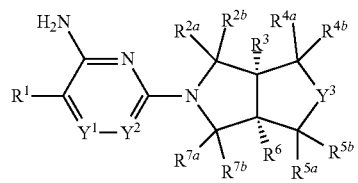

wherein Y¹ is selected from CH and N;
Y² is selected from $CR^{12}$ and N;
Y³ is selected from NH and $CR^8R^9$;
R¹ is selected from (C6-C10)aryl, (C3-C8)cycloalkyl, (C3-C8)cycloalkenyl and a 5-9 membered heteroaryl group containing from 1 to 4 heteroatoms selected from N, O and S; wherein said aryl or heteroaryl is optionally substituted with 1 to 5 $R^{10}$ groups; [0011]$R^{2a}$ and $R^{2b}$ are each independently selected from hydrogen, (C1-C4)alkyl, (C1-C4)alkoxy, amino, hydroxy, (C3-C8)cycloalkyl, (C1-C4)alkyl-amino and di(C1-C4)alkyl-amino;
R³ is hydrogen, fluoro or (C1-C4)alkyl;
$R^{4a}$ and $R^{4b}$ are each independently selected from hydrogen, halo, carbonyl, (C1-C4)alkyl, (C1-C4)alkoxy, amino, hydroxy, (C3-C8)cycloalkyl, (C1-C4)alkylamino and di(C1-C4)alkylamino;
$R^{5a}$ and $R^{5b}$ are each independently selected from are independently selected from hydrogen, halo, carbonyl, (C1-C4)alkyl, (C1-C4)alkoxy, amino, hydroxy, (C3-C8)cycloalkyl, (C1-C4)alkylamino and di(C1-C4)alkylamino;
R⁶ is selected from is hydrogen, fluoro or (C1-C4)alkyl;
$R^{7a}$ and $R^{7b}$ are each independently selected from hydrogen, carbonyl, (C1-C4)alkyl, (C1-C4)alkoxy, amino, hydroxy, (C3-C8)cycloalkyl, (C1-C4)alkylamino and di(C1-C4)alkylamino;
R⁸ is selected from hydrogen, (C1-C4)alkyl, (C3-C6)cycloalkyl, (C6-10)aryl and a 5-9 member heteroaryl group containing from 1 to 4 heteroatoms selected from N, O and S;
R⁹ is selected from $NH_2$, (C1-C4)alkylamino, di(C1-C4)alkylamino, $NH_2$—(CH2)-, (C1-C4)alkyl-NH—(CH2)-, and di[(C1-C4)alkyl]N—(CH2)-;
each $R^{10}$ is independently selected from halo, amino, hydroxy, N3, (C1-C4)alkyl, hydroxy-substituted-(C1-C4)alkyl, halo-substituted-(C1-C4)alkyl, amino-substituted-(C1-C4)alkyl, —C(O)OR¹¹ and —NHC(O)R¹¹;
Each R¹¹ is independently selected from hydrogen, phenyl and naphthyl; wherein said phenyl is optionally substituted with methoxy;
$R^{12}$ is selected from hydrogen, halo, cyano, (C1-C4)alkyl, (C1-C4)alkoxy, amino-carbonyl, halo-substituted (C1-C4)alkyl, halo-substituted (C1-C4)alkoxy, hydroxy-substituted (C1-C4)alkyl, amino-substituted (C1-C4)alkyl, —S(=O)$R^{12a}$, —SO2$R^{12a}$, —C(=S)$R^{12a}$, —C(=O)NR$^{12a}$R$^{12b}$, —C(NH)NR$^{12a}$R$^{12b}$ and —NR$^{12a}$C(=O)R$^{12b}$; wherein each $R^{12a}$ and $R^{12b}$ are independently selected from hydrogen and (C1-C4)alkyl;
or a pharmaceutically acceptable salt thereof.

One aspect of the invention relates to the compounds of Formula I, wherein Y¹ is N; Y² is $CR^{12}$ and $R^{12}$ is hydrogen; Y³ is $CR^8R^9$; and R¹ is (C6-C10)aryl optionally substituted with one or two $R^{10}$ groups.

Another aspect of the invention relates to the compounds of Formula I, wherein each $R^{10}$ group is independently halo.

Another aspect of the invention relates to the compounds of Formula I, wherein each $R^{10}$ group is independently chloro or fluoro.

Another aspect of the invention relates to the compounds of Formula I, wherein Y³ is $CR^8R^9$; and R⁸ is hydrogen or (C1-C4)alkyl.

Another aspect of the invention relates to the compounds of Formula I, wherein Y³ is $CR^8R^9$; and R⁹ is selected from amino, amino-methyl and methyl-amino.

One aspect of the invention relates to the compound

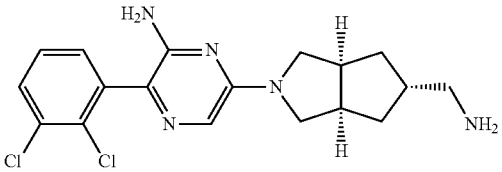 [SMILES: NC[C@H]1C[C@@H]2CN(c3cnc(-c4cccc(Cl)c4Cl)c(N)n3)C[C@@H]2C1]

or a pharmaceutically acceptable salt thereof.

Another embodiment of the invention relates to the compound

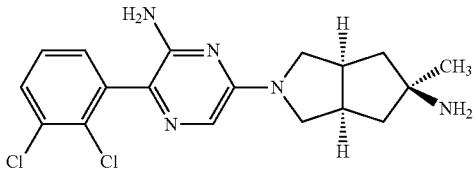 [SMILES: C[C@]1(N)C[C@H]2CN(c3cnc(-c4cccc(Cl)c4Cl)c(N)n3)C[C@H]2C1]

or a pharmaceutically acceptable salt thereof.

Another embodiment of the invention relates to the compound

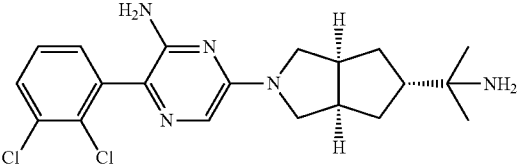 [SMILES: CC(C)(N)[C@H]1C[C@@H]2CN(c3cnc(-c4cccc(Cl)c4Cl)c(N)n3)C[C@@H]2C1]

or a pharmaceutically acceptable salt thereof.

Another embodiment of the invention relates to the compound

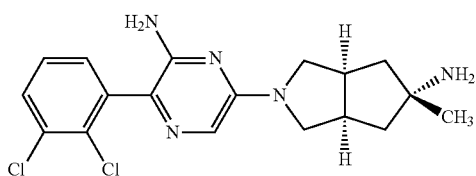 [SMILES: C[C@@]1(N)C[C@H]2CN(c3cnc(-c4cccc(Cl)c4Cl)c(N)n3)C[C@H]2C1]

or a pharmaceutically acceptable salt thereof.

Another embodiment of the invention relates to the compound

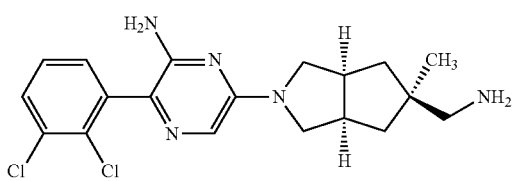 [SMILES: C[C@]1(CN)C[C@H]2CN(c3cnc(-c4cccc(Cl)c4Cl)c(N)n3)C[C@H]2C1]

or a pharmaceutically acceptable salt thereof.

Another embodiment of the invention relates to the compound

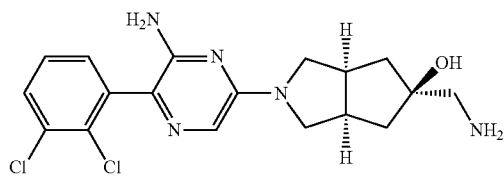 [SMILES: NC[C@]1(O)C[C@H]2CN(c3cnc(-c4cccc(Cl)c4Cl)c(N)n3)C[C@H]2C1]

or a pharmaceutically acceptable salt thereof.

In another aspect, the present invention provides a process for preparing compounds of the invention, prodrug derivatives, protected derivatives, individual isomers and mixture of isomers thereof, and the pharmaceutically acceptable salts thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of the invention can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

General terms used hereinbefore and hereinafter are well understood by those skilled in the art and preferably have within the context of this disclosure the following meanings, unless otherwise indicated, where more general terms wherever used may, independently of each other, be replaced by more specific definitions or remain, thus defining more detailed embodiments of the invention:

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$- includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "C n-m dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$O—. In some embodiments, the two O atoms of a C n-m dialkoxy group may be attached to the same B atom to form a 5- or 6-membered heterocycloalkyl group.

The term "amino" refers to a group of formula —NH$_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CH$_2$F, CCl$_3$, CHCl$_2$, C$_2$Cl$_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3- thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_3$-7). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

In some embodiments related to compounds of Formula I, "alkyl" refers to a fully saturated branched or unbranched hydrocarbon moiety having up to 20 carbon atoms. Unless otherwise provided, alkyl refers to hydrocarbon moieties having 1 to 7 carbon atoms ($C_1$-$C_7$alkyl), or 1 to 4 carbon atoms ($C_1$-$C_4$alkyl). Representative examples of alkyl include, but are not limited to, methyl, ethyl, n-propyl, iso-propyl, n-butyl, sec-butyl, iso-butyl, ten-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three, substituents selected from halogen, hydroxy or alkoxy groups.

In some embodiments related to compounds of Formula I, "carbonyl" as used herein refers to the functionality C═O and includes the aldehyde (H—C═O)—.

In some embodiments related to compounds of Formula I, "halogen" (or halo) preferably represents chloro or fluoro, but may also be bromo or iodo.

In some embodiments related to compounds of Formula I, halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

In some embodiments related to compounds of Formula I, "aryl" means a monocyclic or fused bicyclic aromatic ring assembly containing six to ten ring carbon atoms. For example, aryl may be phenyl or naphthyl, preferably phenyl.

In some embodiments related to compounds of Formula I, "arylene" means a divalent radical derived from an aryl group. The aryl group is optionally substituted by 1 to 5 suitable substituents such as alkyl or halo.

In some embodiments related to compounds of Formula I, "heteroaryl" is as defined for aryl above where one or more of the ring members is a heteroatom. For example (C5-C10) heteroaryl is a minimum of 5 members as indicated by the carbon atoms but that these carbon atoms can be replaced by a heteroatom. Consequently, (C5-C10)heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. The heteroaryl group is optionally substituted by 1 to 5 suitable substituents such as alkyl or halo.

In some embodiments related to compounds of Formula I, "cycloalkyl" means a saturated or partially unsaturated, monocyclic, fused bicyclic or bridged polycyclic ring assembly containing the number of ring atoms indicated. For example, (C3-C10)cycloalkyl includes cyclopropyl, cyclobutyl, cyclopentyl, cyclohexyl, cyclohexenyl, etc. The cycloalkyl group is optionally substituted by 1 to 5 suitable substituents such as alkyl or halo.

In some embodiments related to compounds of Formula I, "heterocycloalkyl" means cycloalkyl, as defined in this application, provided that one or more of the ring carbons indicated, are replaced by a moiety selected from —O—, —N═, —NR—, —C(═O)—, —S—, —S(═O)— or —SO2-, wherein R is hydrogen, (C$_1$-C$_4$)alkyl or a nitrogen protecting group. For example, (C$_3$-C$_8$)heterocycloalkyl as used in this application describes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc. The heterocycloalkyl group is optionally substituted by 1 to 5 suitable substituents such as alkyl or halo.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

The compounds of the invention may have asymmetric carbon atoms and may exist as two or more stereoisomers. The carbon-carbon bonds of compounds of Formula I may be depicted herein using a solid line (⎯), a solid wedge (◢), or a dotted wedge (⋯). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

It will be understood that the compounds of the invention are not limited to the particular enantiomer shown, but also include all stereoisomers and mixtures thereof.

One view of compounds of Formula I has the Formula

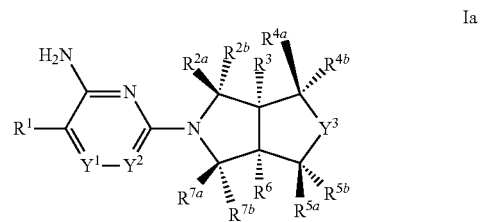

Ia

Stereoisomers include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the the invention may exhibit the phenomena of tautomerism and structural isomerism. For example, the compounds of the invention may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the invention. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

The present invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the compound of the invention, for example, those incorporating a radioactive isotope, are useful in drug and/or substrate tissue distribution studies. The radioactive isotopes tritium, i.e. 3H, and carbon-14, i.e. $^{14}$C, are particularly useful for this purpose in view of their ease of incorporation and ready means of detection. Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagent in place of the non-labeled reagent previously employed. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences, 17th* Ed., (Mack Publishing Company, Easton, 1985), p. 1418, Berge et al., *J. Pharm. Sci.,* 1977, 66(1), 1-19 and in Stahl et al., *Handbook of Pharmaceutical Salts: Properties, Selection, and Use,* (Wiley, 2002). In some embodiments, the compounds described herein include the N-oxide forms.

The compounds of the invention may exist in the form of pharmaceutically acceptable salts such as, e.g., acid addition salts and base addition salts of the compounds of the invention. The phrase "pharmaceutically acceptable salt(s)", as used herein, unless otherwise indicated, includes salts of acidic or basic groups which may be present in the compounds of the invention.

Compounds of the invention are also intended to include N-oxides of such compounds and/or tautomers thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/ chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection*, and Use by Stahl and Wermuth (Wiley-VCH, 2002).

As used herein the terms "Formula I" and "Formula I or pharmaceutically acceptable salts thereof" are defined to include all forms of the compound of Formula I, including hydrates, solvates, isomers, crystalline and non-crystalline forms, isomorphs, polymorphs, metabolites, and prodrugs thereof.

The invention also relates to prodrugs of the compounds of the invention. Thus certain derivatives of compounds of the invention, which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985).

Some non-limiting examples of prodrugs in accordance with the invention include:
(i) where the compound of the invention contains a carboxylic acid functionality which is functionalized into a suitably metabolically labile group (esters, carbamates, etc.);
(ii) where the compound of the invention contains an alcohol functionality which is functionalized into a suitably metabolically labile group (ethers, esters, carbamates, acetals, ketals, etc.); and
(iii) where the compound of the invention contains a primary or secondary amino functionality, or an amide which are functionalized into a suitably metabolically labile group, e.g., a hydrolysable group (amides, carbamates, ureas, phosphonates, sulfonates, etc.).

Further examples of replacement groups in accordance with the foregoing examples and examples of other prodrug types may be found in the aforementioned references.

Moreover, certain compounds of the invention may themselves act as prodrugs of other compounds of the invention.

Also included within the scope of the invention are metabolites of compounds of the invention, that is, compounds formed in vivo upon administration of the drug.

Hereinafter all references to compounds of the invention include references to salts, solvates, multi-component complexes and liquid crystals thereof and to solvates, multi-component complexes and liquid crystals of salts thereof.

The compounds of the invention include compounds of the invention as hereinbefore defined, including all polymorphs and crystal habits thereof, prodrugs and isomers thereof (including optical, geometric and tautomeric isomers) as hereinafter defined and isotopically-labeled compounds of the invention.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry*: Reactions, *Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula A1 can be prepared, for example, according to the process shown in Scheme 1.

Scheme 1

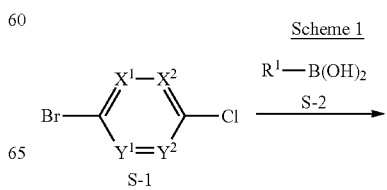

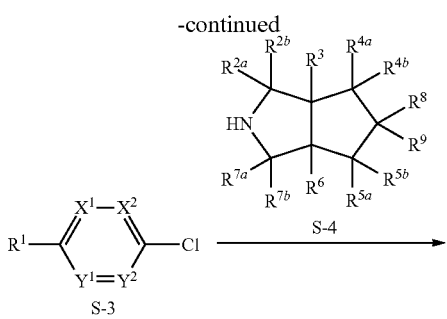

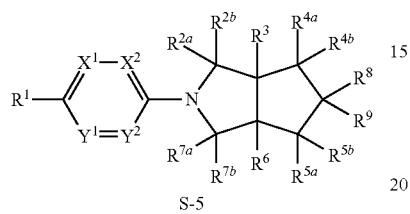

Chloride S-3 can be prepared from the compounds of Formula S-1 and S-2 using a cross coupling, such as Suzuki (e.g., in the presence of a palladacycle precatalyst, such as Xphos Pd G2) or Stille (e.g., in the presence of a palladium catalyst such as $(PPh_3)_2PdCl_2$ and base such as triethylamine). Compound S-3 can then be coupled with amine S-4 in the presence of a base (e.g., cesium carbonate) to afford octahydrocyclopenta[c]pyrrole S-5.

In addition, Compounds described herein may be prepared according to the following reaction schemes and accompanying discussion. Unless otherwise indicated, variables of the above-described Formulas, are as defined above in the reaction schemes and discussion that follow. In general the compounds of this invention may be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section.

As an initial note, in the preparation of the compounds of the invention it is noted that some of the preparation methods useful for the preparation of the compounds described herein may require protection of remote functionality (e.g., primary amine, secondary amine, carboxyl in precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the compound.

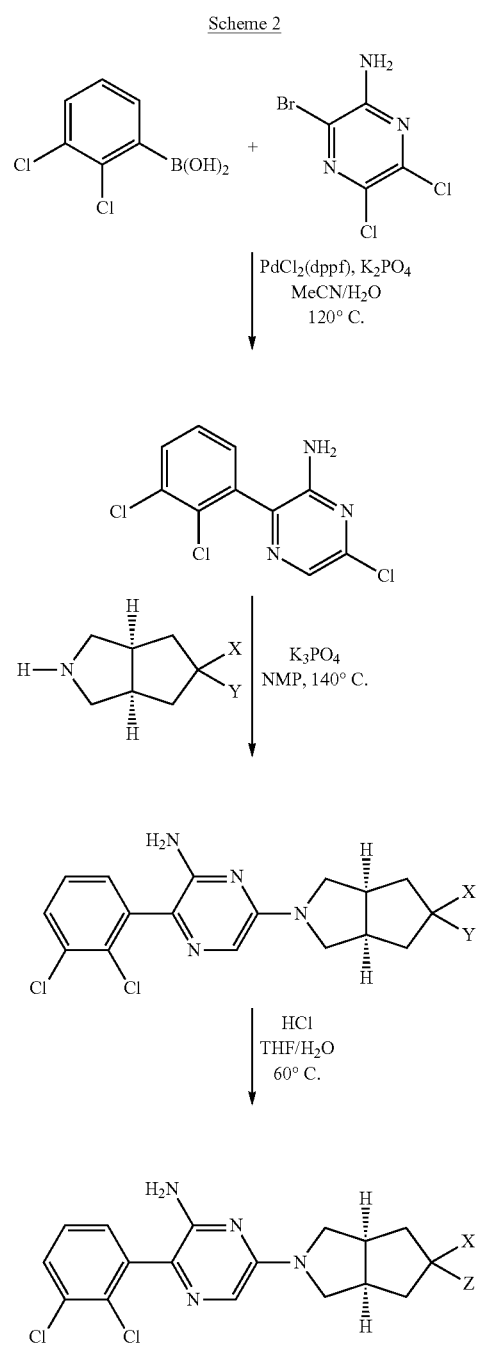

J Med Chem 2016, 59, 7773-7782

Scheme 3
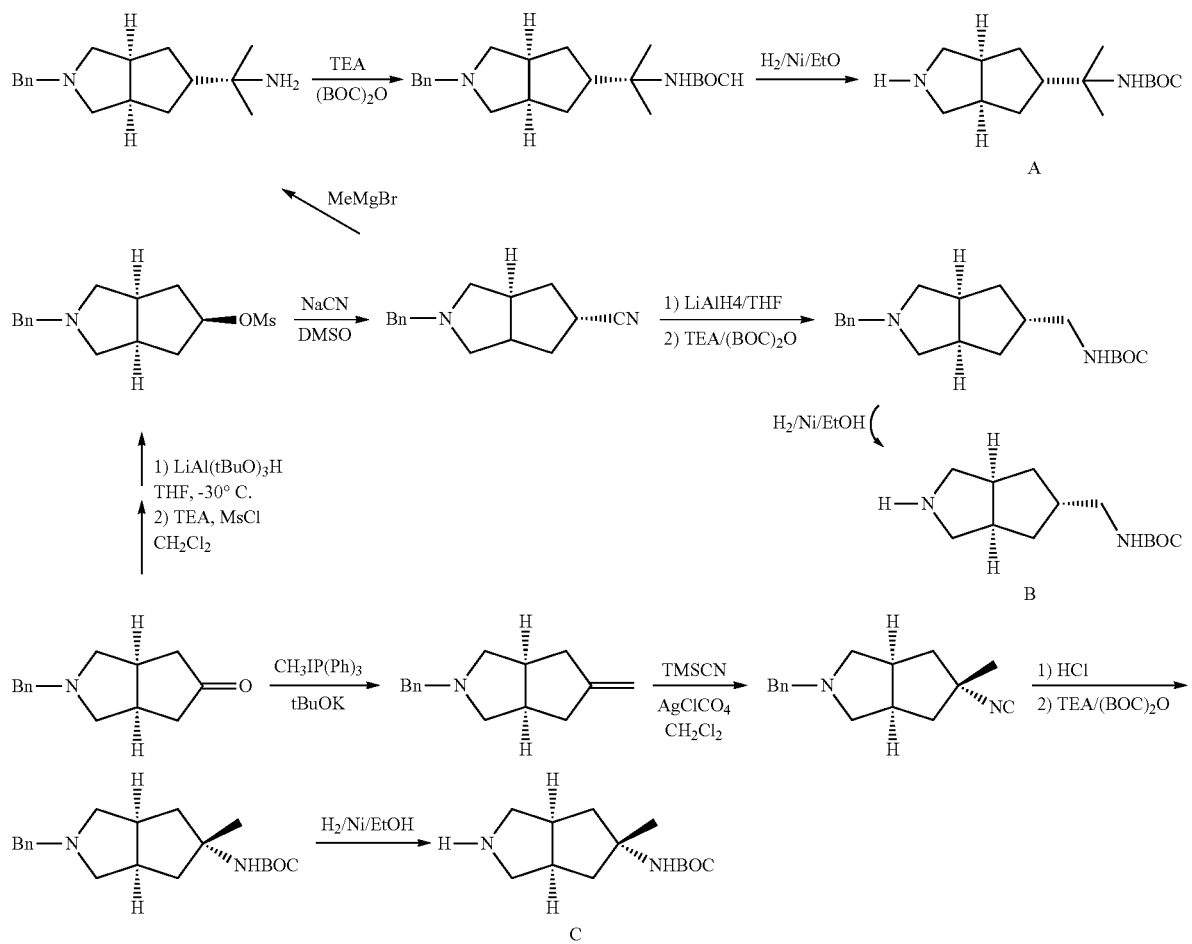
Scheme 4
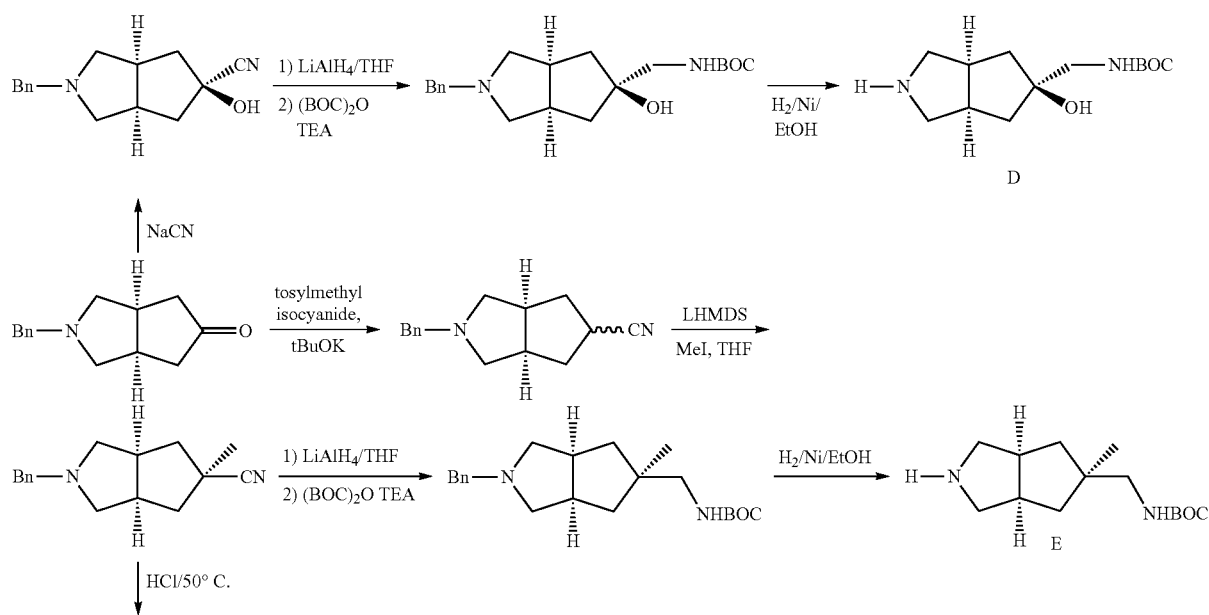

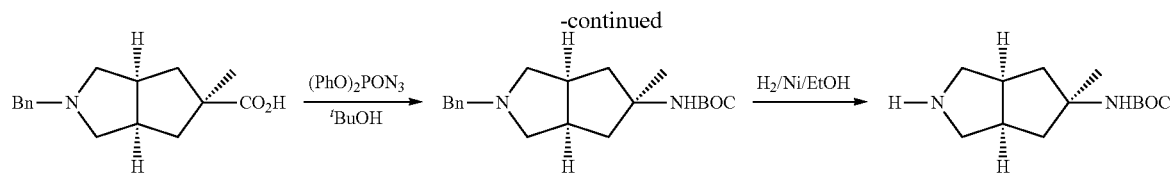

Bioorg Med Chem Lett 2010, 20, 3565-3568

Referring to Scheme 2, it is understood that the coupling between the borate and halo-pyrazine is generic, encompassing the $R^1$ and $Y^1$ and $Y^2$ scope. Likewise X and Z is intended to cover the scope of R8 and R9.

Schemes 3 and 4 generically describe the preparation of A-F intermediates that can be be converted to final products by methods well known to those skilled in the art.

Compounds of the invention that have chiral centers may exist as stereoisomers, such as racemates, enantiomers, or diastereomers. Conventional techniques for the preparation/ isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Compounds that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the invention. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In some embodiments, the pharmaceutically acceptable salt is a hydrochloric acid salt, which includes, for example, hemihydrochloric acid salts, monohydrochloric acid salts, dihydrochloric acid salts, etc.

Pharmaceutically acceptable salts of compounds of the invention may be prepared by one or more of three methods:
  (i) by reacting the compound of the invention with the desired acid or base;
  (ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

Polymorphs can be prepared according to techniques well-known to those skilled in the art.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The invention also includes isotopically-labeled compounds of the invention, wherein one or more atoms is replaced by an atom having the same atomic number, but an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985).

SHP2

The present disclosure provides methods of modulating (e.g., inhibiting) SHP2 activity, by contacting SHP2 with a compound of the invention, or a pharmaceutically acceptable salt thereof. In some embodiments, the contacting can be administering to a patient a compound provided herein, or a pharmaceutically acceptable salt thereof.

In another aspect, the present invention provides a method of treating a disease in an animal, preferably a human, in which modulation of SHP2 activity can prevent, inhibit or ameliorate the pathology and/or symptomology of the diseases, which method comprises administering to the animal, preferably a human, a therapeutically effective amount of a compound of the invention or a pharmaceutically acceptable salt thereof. The compounds of the present disclosure can be used alone, in combination with other agents or therapies or as an adjuvant or neoadjuvant for the treatment of diseases. For the uses described herein, any of the compounds of the disclosure, including any of the embodiments thereof, may be used.

In another aspect, the present invention provides the use of a compound of the invention in the manufacture of a medicament for treating a disease in an animal in which SHP2 activity contributes to the pathology and/or symptomology of the disease.

"SHP2" as used herein means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y; D61Y, V; E69K; A72V, T, D; E76G, Q, K (ALL); G60A; D61Y; E69V; F71K; A72V; T73I; E76G, K; R289G; G503V (AML); G60R, D61Y, V, N; Y62D; E69K; A72T, V; T73I; E76K, V, G, A, Q; E139D; G503A, R; Q506P (JMML); G60V; D61V; E69K; $F_{71}L$; A72V; E76A (MDS); Y63C (CMML); Y62C; E69K; T507K (neuroblastoma); V46L; N58S; E76V (Lungcancer); R138Q (melanoma); E76G (colon cancer).

In another aspect, the present invention provides a method of treating a disease in an animal, preferably a human, in which modulation of SHP2 activity can prevent, inhibit or ameliorate the pathology and/or symptomology of the diseases, which method comprises administering to the animal, preferably a human, a therapeutically effective amount of a compound of the invention or a pharmaceutically acceptable salt thereof, in simultaneous or sequential combination with an anti-cancer therapeutic.

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N—SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, Crouzon Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Diseases and disorders treatable or preventable by administration of the compounds of the invention to a patient in need thereof include, for example, Noonan Syndrome, Leopard Syndrome, Crouzon Syndrome, Jackson-Weiss syndrome, Beare-Stevenson cutis gyrate, Apert syndrome, Pfeiffer syndrome, Muenke syndrome, Saethre-Chotzen-like syndrome, achondroplasia, SADDAN (severe achondroplasia with developmental delay and acanthosis nigricans), thanatophoric dysplasia type I, thanatophoric dysplasia type II, hypochondroplasia, Kallmann syndrome, myeloproliferative syndromes, juvenile myelomonocytic leukemias, multiple myeloma, 8P11 myeloproliferative syndrome (EMS), pancreatic adenocarcinoma, prostate cancer, astrocytoma, transitional cell carcinoma of bladder, thyroid carcinoma, cervical carcinoma, colorectal cancer, peripheral T cell lymphoma, seminomas, neuroblastoma, melanoma, acute myeloid leukemia, chronic myelogenous leukemia, breast cancer, esophageal cancer, lung cancer, colon cancer, head cancer, squamous-cell carcinoma of the head and neck, gastric carcinoma, anaplastic large-cell lymphoma and glioblastoma.

Noonan Syndrome (NS) and Leopard Syndrome (LS)—PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germ-line mutations in PTPN11 (SHP2) are found in about. 50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Crouzon syndrome is an autosomal dominant genetic disorder known as a branchial arch syndrome. This syndrome affects the first branchial (or pharyngeal) arch, which is the precursor of the maxilla and mandible. Since the branchial arches are important developmental features in a growing embryo, disturbances in their development create lasting and widespread effects.

Juvenile Myelomonocytic Leukemias (JMML)—Somatic mutations in PTPN11 (SHP2) occur in about 35% of the patients with JMML, a childhood myeloproliferative disorder (MPD).

These gain-of-function mutations are typically point mutations in the N—SH2 domain or in the phosphatase domain, which prevent self-inhibition between the catalytic domain and the N—SH2 domain, resulting in SHP2 activity.

Acute Myeloid Leukemia—PTPN11 mutations have been identified in: about 10% of pediatric acute leukemias, such as myelodysplastic syndrome (MDS); about 7% of B cell acute lymphoblastic leukemia (B-ALL); and about 4% of acute myeloid leukemia (AML).

NS and leukemia mutations cause changes in amino acids located at the interface formed by the N—SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations ($EGFR^{amp}$, $Her2^{amp}$, $FGFR^{amp}$, $Met^{amp}$, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a maj or type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality. accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastic Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastomapathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

In another aspect, the present invention relates to compounds capable of inhibiting the activity of SHP2.

In another aspect, the present invention relates to processes for the preparation of compounds of the invention and pharmaceutical preparations comprising such compounds.

Another aspect of the present invention relates to a method of treating SHP2-mediated disorders comprising the step of administering to a patient in need thereof a therapeutically effective amount of a compound of the invention.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

In another aspect, the present invention relates to the use of a compound of the invention (or a pharmaceutical composition comprising a compound of the invention) in the treatment of one or more of the diseases mentioned herein; wherein the response to treatment is beneficial as demonstrated, for example, by the partial or complete removal of one or more of the symptoms of the disease up to complete cure or remission.

As used herein, the term "contacting" refers to the bringing together of the indicated moieties in an in vitro system or an in vivo system such that they are in sufficient physical proximity to interact.

The terms "individual" or "patient," used interchangeably, refer to any animal, including mammals, preferably mice, rats, other rodents, rabbits, dogs, cats, swine, cattle, sheep, horses, or primates, and most preferably humans.

The term "therapeutically effective amount" as used herein refers to that amount of the compound being administered which will relieve to some extent one or more of the symptoms of the disorder being treated. In reference to the treatment of an SHP2 Mediated Disease such as cancer, a therapeutically effective amount refers to that amount which has the effect of inhibiting the phosphatase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. The term "treating" or "treatment" can also refer to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

In another aspect, the present invention relates to SHP2 inhibitor(s) of the present invention usefully combined with another pharmacologically active compound, or with two or more other pharmacologically active compounds, particularly in the treatment of cancer. For example, a compound of the invention, or a pharmaceutically acceptable salt thereof, as defined above, may be administered simultaneously, sequentially or separately in combination with one or more agents selected from chemotherapy agents, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In another aspect, the present invention relates to a method of treating an SHP2-mediated disorder, comprising the step of: administering to a patient in need thereof a therapeutically effective amount of a chemothereutic agent in combination with a therapeutically effective amount of a compound of of the invention.

In another aspect, the present invention relates to a compound of the invention in combination with the following compounds:

BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INN0406); Danusertib (PHA-739358), AT9283 (CAS 1133385-83-7);

Saracatinib (AZD0530); andN-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3); and LGX818.

ALK inhibitors: PF-2341066 (XALKORI®; crizotinib); 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine; GSK1838705A; and $CH_{5424802}$.

BRAF inhibitors: Vemurafanib (PLX4032); and Dabrafenib.

FLT3 inhibitors-sunitinib malate (sold under the tradename Sutent® by Pfizer); and PKC412 (midostaurin).

MEK Inhibitors-trametinib.

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AGO13736, and described in PCT Publication No. WO 01/002369), Brivanib Alaninate ((S)-((R)-1-(4-(4-Fluoro-2-methyl-1H-indol-5-yloxy)-5-methyl-pyrrolo[2,1-f][1,2,4]triazin-6-yloxy)propan-2-yl)$_2$-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline);

D20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R,3S,4R,5R)-2-(2-amino-6-methoxypurin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen); HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C$_6$, available from Seattle Genetics, Inc);

Pro-apoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors: 4-[2-(1H-Indazol-4-yl)-6-[[4-(methylsulfonyl)piperazin-1-yl]methyl]thieno-[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]-quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-pipera-zinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0-.sup.4,9]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor .kappa. B (RANK) inhibitors: Denosumab (sold under the tradename Prolia® by Amgen);

Thrombopoietin mimetic peptibodies: Romiplostim (sold under the tradename Nplate® by Amgen);

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®;

Biologic response modifiers: bacillus calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence®), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-N.sup.2-{(1S)-2,2,2-trifluoro-1-[4'-(meth-ylsulfonyl)biphenyl-4-yl]ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-73,1013-dimethoxy-9-oxo-5 β,20-epoxytax-11-ene-2-α,4,13α-triyl-4-acetate-2-benzoate-13-[(2R,3S)-3-{[(tert-butoxy-)carbonyl]amino}-2-hydroxy-3-phenylpropanoate), larotaxel ((2α,3ξ,4α,5β,7α,10β, 13α)-4,10-bis(acetyloxy)-13-({(2R,3S)-3-[(tert-butoxycarbonyl) amino]-2-hydroxy-3-phenylpropanoyl)}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl)phenyl]-1,2,3,6-tetrahydropyridine, and described in U.S. Pat. No. 5,266,573);

HPC vaccines: Cervarix® sold by GlaxoSmithKline, Gardasil® sold by Merck;

Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosyl-cytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and VincasarPfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cy-clopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Estrogen receptor downregulators: Fulvestrant (sold under the tradename Faslodex®);

Anti-estrogens: tamoxifen (sold under the tradename Novaldex®);

Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®);

In another aspect, the present invention relates to a compound of the invention in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

When more than one pharmaceutical agent is administered to a patient, they can be administered simultaneously, separately, sequentially, or in combination (e.g., for more than two agents).

Formulation, Dosage Forms and Administration

When employed as pharmaceuticals, the compounds of the present disclosure can be administered in the form of pharmaceutical compositions. Thus the present disclosure provides a composition comprising a compound of Formula I, Formula A1, or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

In another aspect, the present invention relates to the aforementioned method, wherein said compound is administered parenterally.

In another aspect, the present invention relates to the aforementioned method, wherein said compound is administered intramuscularly, intravenously, subcutaneously, orally, pulmonary, intrathecally, topically or intranasally.

In another aspect, the present invention relates to the aforementioned method, wherein said compound is administered systemically.

In another aspect, a first dose is administered in utero (either directly or to the mother).

In certain aspects, the first dose is administered prior to complete formation of the blood-brain-barrier. In other aspects, a first dose is administered within 1 week of birth of the subject. In other aspects, a first dose is administered within 1 month of birth of the subject. In other aspects, a first dose is administered within 3 months of birth of the subject. In other aspects, a first dose is administered within 6 months of birth of the subject.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

The compounds of the invention should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

The compounds of the invention may also be used in fast-dissolving, fast-disintegrating dosage forms such as those described in Expert Opinion in Therapeutic Patents, 11 (6), 981-986, by Liang and Chen (2001).

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan.

Determining appropriate dosages and regimens for administration of the active agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician.

However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of the invention, a film-forming polymer, a binder, a solvent, a humectant, a plasticiser, a stabiliser or emulsifier, a viscosity-modifying agent and a solvent.

Some components of the formulation may perform more than one function.

The compounds of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of the invention may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.05 g to 1 g of the compound of the invention.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of the invention, a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. In addition, the liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The compounds of the invention can also be coupled to suitable carriers to improve delivery, stability, and/or efficacy when administered to a patient.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed below are only illustrative of the invention. It should be understood that various modifications can be made without departing from the spirit of the invention. Accordingly, the invention is limited only by the claims.

In the following Examples and Preparations, "BOC", "Boc" or "boc" means N-tert-butoxycarbonyl, "DCM" (CH$_2$Cl$_2$) means methylene chloride, "DIPEA" or "DIEA" means diisopropyl ethyl amine, "DMA" means N,N-dimethylacetamide, "DMF" means N—N-dimethyl formamide, "DMSO" means dimethylsulfoxide, "DPPP" means 1,3-bis(diphenylphosphino)propane, "HOAc" means acetic acid, "IPA" means isopropyl alcohol. "MTBE" means methyl t-butyl ether, "NMP" means 1-methyl 2-pyrrolidinone, "TEA" means triethyl amine, "TFA" means trifluoroacetic acid, "DCM" means dichloromethane, "EtOAc" means ethyl acetate, "MgSO$_4$" means magnesium sulphate, "NaSO$_4$" means sodium sulphate, "MeOH" means methanol, "EtOH" means ethanol, "H$_2$O" means water, "HCl" means hydrochloric acid, "POCl$_3$" means phosphorus oxychloride, "DMSO" means dimethyl sulfoxide, "K$_2$CO$_3$" means potassium carbonate, "N" means Normal, "M" means molar, "mL" means milliliter, "mmol" means millimoles, "tmol" means micromoles, "eq." means equivalent, "° C." means degrees Celsius, "Pa" means pascals.

EXAMPLES

Yields reported herein refer to purified products (unless specified). Analytical TLC was performed on Merck silica gel 60 F$_{254}$ aluminium-backed plates. Compounds were visualised by UV light and/or stained with iodine, ninhydrin or potassium permanganate solution followed by heating. Flash column chromatography was performed on silica gel. $^1$H-NMR spectra were recorded on a Bruker 400 MHz, Avance II spectrometer with a 5 mm DUL (Dual) 13C probe and Bruker 400 MHz, Avance III HD spectrometer with BBFO (Broad Band Fluorine Observe) probe. Chemical shifts (δ) are expressed in parts per million (ppm) with reference to the deuterated solvent peak in which the sample is prepared. Splitting patterns are designated as s (singlet), d (doublet), t (triplet), q (quartet), m (multiplet) and bs (broad singlet).

The following solvents, reagents or scientific terminology may be referred to by their abbreviations:
TLC Thin Layer Chromatography
mL Milliliters
mmol Millimoles
h Hour or hours
min Minute or minutes
g Grams
mg Milligrams
eq Equivalents
rt or RT Room temperature, ambient temperature, or about 25° C.
MS Mass spectrometry
SMs Starting material Intermediates A and B Synthesis of tert-butyl ((3aR,5s,6aS)-5-methyloctahydrocyclopenta[c]pyrrol-5-yl)carbamate (Intermediate A) and tert-butyl ((3aR,5r,6aS)-5-methyloctahydrocyclopenta[c]pyrrol-5-yl)carbamate (Intermediate B)

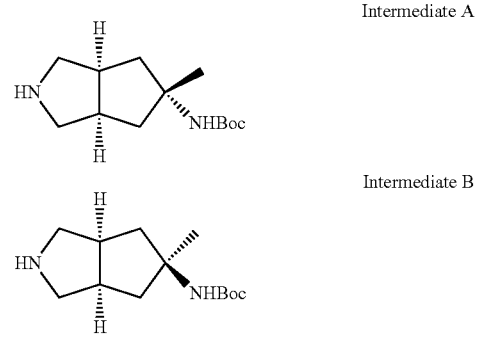

Step 1: Synthesis of 2,3,3a,4,7,7a-hexahydro-H-isoindole

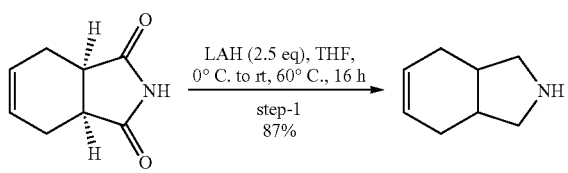 [SMILES: O=C1NC(=O)[C@@H]2CC=CC[C@H]12 ; "LAH (2.5 eq), THF,0° C. to rt, 60° C., 16 h" ; C1=CCC2CNCC2C1]

To a stirred solution of lithium aluminum hydride (44 g, 1.15 mol) in THF (2.2 L) at 0° C., a solution of 3a,4,7,7a-tetrahydro-1H-isoindole-1,3(2H)-dione (70 g, 0.46 mol) in THF (500 mL) was added drop wise. The reaction mixture was allowed to stir at 60° C. for 12 h. After consumption of starting materials as observed by TLC, the reaction mixture was cooled to 0° C. and quenched with THF:water (70 mL, 9:1) followed by 15% aq. solution of NaOH (70 mL) and water (140 mL) over 2 h. The rate of quenching was done carefully so as to maintain an internal temperature below 25° C. The resulting mixture was stirred at rt for 1 h and filtered through celite bed followed by washing with DCM (3×300 mL). The collected filtrate was concentrated under reduced pressure to afford 2,3,3a,4,7,7a-hexahydro-1H-isoindole (50 g, 87% yield) as brown semi-solid.
MS (ESI+ve): 124.0
$^1$H NMR (400 MHz, CDCl$_3$) δ 5.29 (s, 2H), 3.88 (bs, 1H), 3.26 (m, 2H), 2.82 (m, 2H), 2.41-2.19 (m, 4H), 1.96 (m, 2H).

Step 2: Synthesis of benzyl 1,3,3a,4,7,7a-hexahydro-2H-isoindole-2-carboxylate

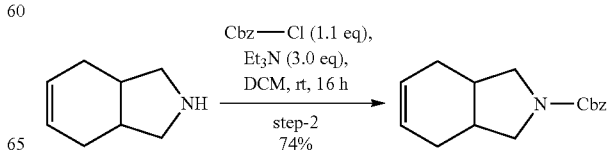

To a stirred solution of 2,3,3a,4,7,7a-hexahydro-1H-isoindole (90 g, 0.73 mol) in DCM (2 L) were added Et₃N (316 mL, 2.19 mol) and Cbz-Cl (135 mL) at 0° C. The reaction mixture was stirred at rt for 16 h. Progress of reaction was monitored by TLC, which showed consumption of starting material. The reaction mixture was diluted with ice cold water (500 mL) and extracted with EtOAc (3×500 mL). The organic layer was separated, washed with brine (500 mL), dried (Na₂SO₄), filtered and concentrated to dryness. The residue was purified by column chromatography using silica gel (100-200 mesh), gradient 20% EtOAc in hexane to afford benzyl 1,3,3a,4,7,7a-hexahydro-2H-isoindole-2-carboxylate (140 g, 74%) as a brown semi-solid.

MS (ESI+ve): 258.08

¹H-NMR (400 MHz; DMSO-d₆): δ 7.31-7.42 (m, 5H), 5.62 (s, 2H), 5.05 (s, 2H), 3.38-3.43 (m, 2H), 3.02-3.07 (m, 2H), 2.18-2.22 (m, 4H), 1.79-1.82 (m, 2H).

Step 3: Synthesis 2,2'-(1-((benzyloxy)carbonyl)pyrrolidine-3,4-diyl)diacetic acid

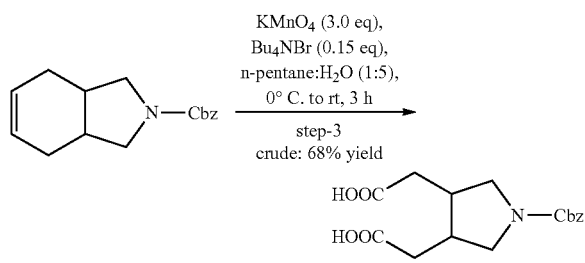

To a stirred solution of benzyl 1,3,3a,4,7,7a-hexahydro-2H-isoindole-2-carboxylate (130 g, 0.50 mol) in pentane (2 L) was added a solution of potassium permanganate (239 g, 1.51 mol) and tetrabutyl ammonium bromide (24.4 g, 0.077 mol) in water (600 mL) at 0° C. The resulting suspension was allowed to stir at rt for 3 h. Progress of reaction was monitored by TLC, which showed consumption of starting material. The reaction mixture was filtered through a celite bed and the bed was washed with water (2 L). The combined filtrate was washed with ethyl acetate (1 L) and the organic layer was separated. The collected aqueous layer was acidified with 1N hydrochloric acid solution to adjust pH~1 and extracted with ethyl acetate (3×1 L). The combined organic layer was washed with brine, dried over Na₂SO₄, filtered and concentrated under reduced pressure to furnish 2,2'-(1-((benzyloxy)carbonyl)pyrrolidine-3,4-diyl)diacetic acid (132 g, crude) as brown semisolid, which was used for next step without further purification.

MS (ESI+ve): 322.15

Step 4: Synthesis of benzyl 5-oxohexahydrocyclopenta[c]pyrrole-2(1H)-carboxylate

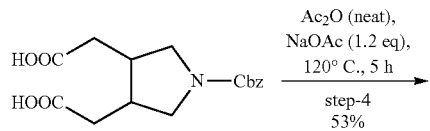

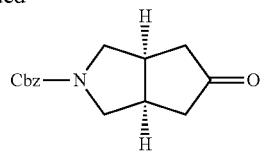

To a stirred solution of 2,2'-(1-((benzyloxy)carbonyl)pyrrolidine-3,4-diyl)diacetic acid (132 g, 0.411 mol) in acetic anhydride (1.3 L) was added sodium acetate (40.4 g, 0.493 mol) under inert atmosphere and resulting suspension was stirred at 120° C. for 5 h. Progress of reaction was monitored by TLC, which showed consumption of starting material. The reaction mixture was allowed to cool to rt and solids material was separated out through filtration followed by washing with ethyl acetate (500 mL). The combined filtrate was concentrated under vacuum to get crude material which was purified by column chromatography using 100-200 mesh silica gel and 30% ethyl acetate/hexane as eluent to afford benzyl 5-oxohexahydrocyclopenta[c]pyrrole-2(1H)-carboxylate (57 g, 53%) as an off white solid.

MS (ESI+ve): 260.2

¹H-NMR (400 MHz; DMSO-d₆): δ 7.30-7.36 (m, 5H), 5.05 (s, 2H), 3.59-3.62 (m, 2H), 3.17-3.20 (m, 2H), 2.89 (s, 2H), 2.37-2.42 (m, 2H), 2.07-2.12 (m, 2H).

Step 5. Synthesis of benzyl 5-hydroxyhexahydrocyclopenta[c]pyrrole-2(1H)-carboxylate

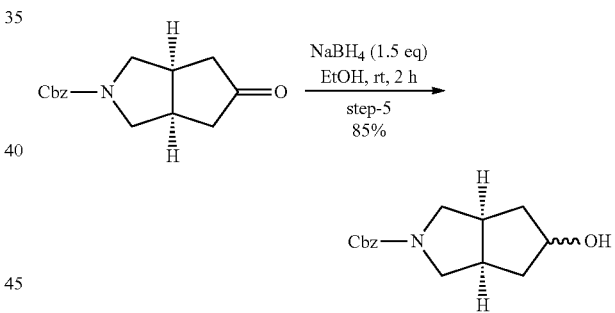

To a stirred solution of benzyl 5-oxohexahydrocyclopenta[c]pyrrole-2(1H)-carboxylate (39.6 g, 0.15 mol) in EtOH (650 mL), sodium borohydride (9.8 g, 0.26 mol) was added portion wise under argon atmosphere at 0° C. The reaction mixture was stirred at rt for 2 h. Progress of reaction was monitored by TLC, which showed consumption of starting material. The reaction mixture was concentrated under reduced pressure to dryness, diluted with ice cold water (550 mL) and extracted with EtOAc (3×350 mL). The combined organic layer was washed with brine (500 mL), dried (Na₂SO₄), filtered and evaporated in vacuum to afford benzyl 5-hydroxyhexahydrocyclopenta[c]pyrrole-2(1H)-carboxylate (44.1 g, crude) as a brown semi-solid.

MS (ESI+ve): 262.19

¹H-NMR (400 MHz; DMSO-d₆): δ 7.31-7.36 (m, 5H), 5.05 (s, 2H), 4.60-4.63 (m, 1H), 3.42-3.48 (m, 2H), 3.30-3.33 (m, 2H), 2.54-2.59 (m, 2H), 1.97-2.08 (m, 2H), 1.29-1.35 (m, 2H).

Step 6. Synthesis of benzyl 5-((methylsulfonyl)oxy) hexahydrocyclopenta[c]pyrrole-2(1H)-carboxylate

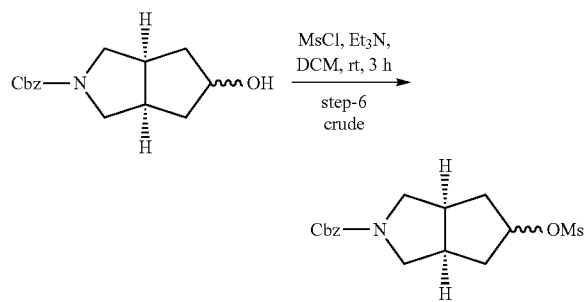

To a stirred solution of benzyl 5-hydroxyhexahydrocyclopenta [c]pyrrole-2(1H)-carboxylate (44 g, 0.16 mol) in DCM (700 mL), were added Et$_3$N (70 mL, 0.50 mol) and MsCl (26 mL, 0.33 mol) drop wise under argon atmosphere at 0° C. The reaction mixture was allowed to stir at rt for 3 h. Progress of reaction was monitored by TLC, which showed consumption of starting material. The reaction mixture was diluted with ice cold water (550 mL) and extracted with DCM (3×350 mL). The combined organic layer was washed with brine (300 mL), dried (Na$_2$SO$_4$), filtered and evaporated under vacuum to afford benzyl 5-((methylsulfonyl)oxy) hexahydrocyclopenta[c]pyrrole-2(1H)-carboxylate (55.6 g, crude) as a brown semi-solid. This was used for next step without further purification.

MS (ESI+ve): 340.2

$^1$H-NMR (400 MHz; DMSO-d$_6$): δ 7.31-7.36 (m, 5H), 5.05 (s, 2H), 3.48-3.53 (m, 2H), 3.29-3.33 (m, 3H), 3.13 (s, 3H), 2.65-2.69 (m, 2H), 2.26-2.29 (m, 2H), 1.68-1.74 (m, 2H).

Step 7: Synthesis of benzyl 5-cyanohexahydrocyclopenta[c]pyrrole-2(1H)-carboxylate

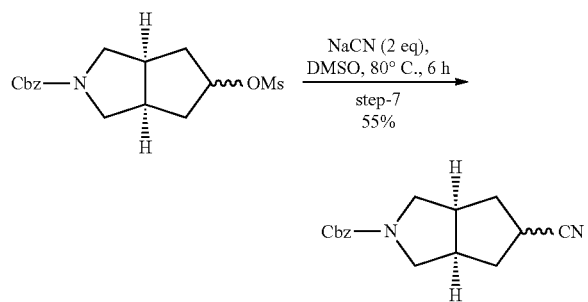

To a stirred solution of benzyl 5-((methylsulfonyl)oxy) hexahydro cyclopenta[c]pyrrole-2(1H)-carboxylate (55 g, 0.16 mol) in DMSO (850 mL), NaCN (23.8 g, 0.48 mol) was added to it. The reaction mixture was stirred at 80° C. for 6 h. Progress of reaction was monitored by TLC, which showed consumption of starting material. The resulting mixture was diluted with ice cold water (850 mL) and extracted with EtOAc (3×350 mL). The combined organic layer was washed with brine (500 mL), dried (Na$_2$SO$_4$), filtered and concentrated to dryness. The crude residue was purified by column chromatography using 15% EtOAc in hexane to afford benzyl 5-cyanohexahydrocyclopenta[c]pyrrole-2(1H)-carboxylate (27 g, 61%) as an off-white solid.

MS (ESI+ve): 271.15

$^1$H-NMR (400 MHz; DMSO-d$_6$): δ 7.31-7.35 (m, 5H), 5.03 (s, 2H), 3.48-3.53 (m, 2H), 3.17-3.20 (m, 1H), 3.08-3.13 (m, 2H), 2.79-2.83 (m, 2H), 1.97-2.03 (m, 2H), 1.88-1.92 (m, 2H).

Step 8. Synthesis of benzyl 5-cyano-5-methylhexahydrocyclopenta[c]pyrrole-2(1H)-carboxylate

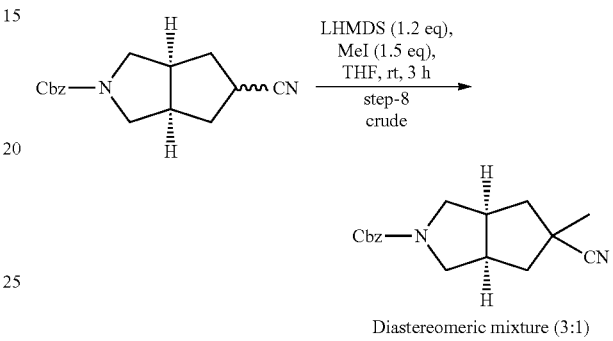

Diastereomeric mixture (3:1)

To a stirred solution of benzyl 5-cyanohexahydrocyclopenta[c]pyrrole-2(1H)-carboxylate (27 g, 0.10 mol) in THF (900 mL), LiHMDS (120 mL, 0.12 mol, 1M in THF) was added at −78° C. drop wise over 15 min. The reaction mass was stirred for 30 min then MeI (18.4 g, 0.13 mol) was added. The resulting mixture was stirred for another 2 h at rt. Progress of reaction was monitored by TLC, which showed consumption of starting material. The reaction mixture was diluted with water (500 mL) and extracted with EtOAc (3×150 mL). The organic layer was separated, washed with brine (300 mL), dried (Na$_2$SO$_4$), filtered and concentrated to dryness to afford benzyl 5-cyano-5-methylhexahydrocyclopenta[c]pyrrole-2(1H)-carboxylate (27.5 g, crude) as a brown semi-solid which was mixture of diastereomers (ratio ~3:1 through LCMS) and used for next step without further purification.

MS (ESI+ve): 285.12

$^1$H-NMR (400 MHz; DMSO-d$_6$): δ 7.31-7.35 (m, 5H), 5.05 (s, 2H), 3.48-3.53 (m, 2H), 3.27-3.30 (m, 2H), 2.79-2.83 (m, 2H), 1.98-2.03 (m, 2H), 1.87-1.90 (m, 2H), 1.31 (s, 3H).

Step 9 & 10: Synthesis of 2-((benzyloxy)carbonyl)-5-methyloctahydrocyclopenta[c]pyrrole-5-carboxylic acid

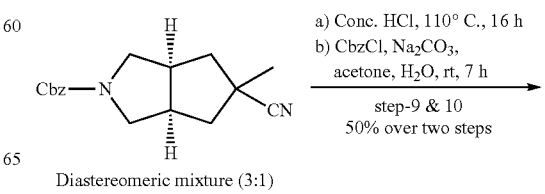

Diastereomeric mixture (3:1)

-continued

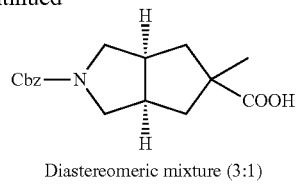

Diastereomeric mixture (3:1)

A solution of benzyl 5-cyano-5-methylhexahydro cyclopenta[c]pyrrole-2(1H)-carboxylate (27 g, 0.09 mol) in conc. HCl (60 mL) was heated at 110° C. for 16 h. Progress of reaction was monitored by TLC, which showed consumption of starting material. The reaction mixture was concentrated to dryness to get residue, which was was dissolved in acetone/water (30 mL, 1:1) and added $Na_2CO_3$ (49.9 g, 0.47 mol) followed by Cbz-Cl (17.5 mL, 0.12 mol) at 0° C. The reaction mixture was stirred at rt for 7 h. After consumption of starting materials as observed by TLC, the reaction mixture was concentrated in vacuum to remove acetone, washed with EtOAc (3×250 mL) to remove non polar impurities. The aqueous layer was acidified with citric acid (pH~3) and extracted with DCM (5×50 mL). The organic layer was separated, washed with brine (300 mL), dried ($Na_2SO_4$), filtered and evaporated in vacuum to afford 2-((benzyloxy)carbonyl)-5-methyloctahydrocyclopenta[c]pyrrole-5-carboxylic acid (14 g, crude) as an off white solid as mixture of diastereomers (ratio ~3:1 though LCMS) and used for next step without further purification.

MS (ESI–ve): 302.0

$^1$H-NMR (400 MHz; DMSO-$d_6$): δ 12.19 (s, 1H), 7.31-7.35 (m, 5H), 5.05 (s, 2H), 3.39-3.44 (m, 2H), 3.18-3.24 (m, 2H), 2.71-2.75 (m, 2H), 2.64-2.66 (m, 1H), 2.31-2.35 (m, 1H), 1.83-1.86 (m, 2H), 1.72-1.78 (m, 2H), 1.23 (s, 1H), 1.19 (s, 3H).

Step 11: Synthesis of benzyl 5-(azidocarbonyl)-5-methylhexahydrocyclopenta[c]pyrrole-2(1H)-carboxylate

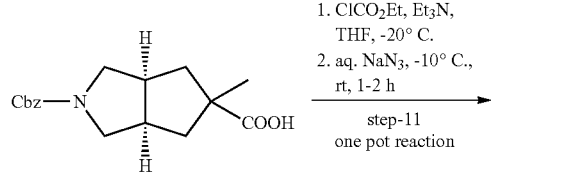

To a stirred solution of 2-((benzyloxy)carbonyl)-5-methyloctahydro cyclopenta[c]pyrrole-5-carboxylic acid (14.1 g, 0.04 mol) in THF (280 mL) were added $Et_3N$ (16.2 mL, 0.11 mol) and ethylchloroformate (6.64 mL, 0.06 mol) at −20 OC drop wise. The reaction mass was stirred for 10 min at −20° C. then a solution of $NaN_3$ (7.56 g, 0.11 mol) in water (30 mL) was added drop wise. The resulting mixture was stirred for 1 h at rt. Progress of reaction was monitored by TLC, which showed consumption of starting material. The reaction mixture was diluted with water (250 mL) and extracted with EtOAc (3×150 mL). The organic layer was separated, washed with brine (200 mL), dried ($Na_2SO_4$), filtered and evaporated in vacuum to afford benzyl 5-(azidocarbonyl)-5-methylhexahydrocyclopenta[c]pyrrole-2(1H)-carboxylate (13.3 g, crude) as a semi-solid as mixture of diastereomers (~3:1 ratio) and used for next step without further purification.

MS (ESI+ve): 329.1

Steps 12 & 13: Synthesis of benzyl (3aR,5s,6aS)-5-((tert-butoxycarbonyl) amino-5-methylhexahydro cyclopenta[c]pyrrole-2(1H)-carboxylate & benzyl (3aR,5r,6aS)-5-((tert-butoxy carbonyl)amino)-5-methylhexahydro cyclopenta[c]pyrrole-2(1H)-carboxylate

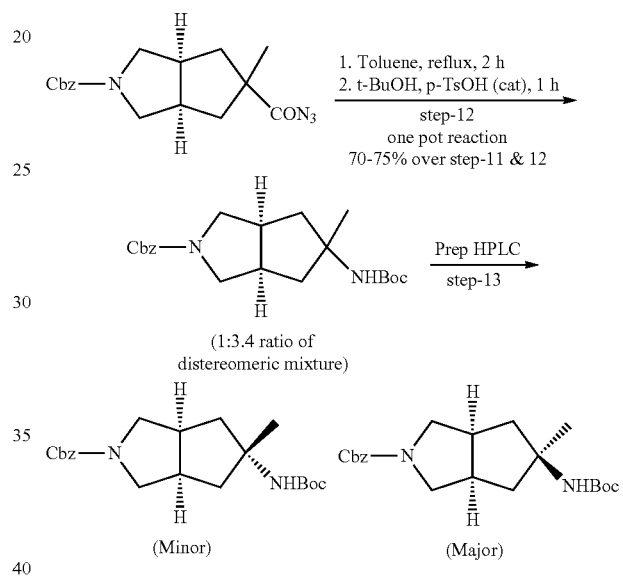

A solution of benzyl 5-(azidocarbonyl)-5-methylhexahydrocyclopenta [c]pyrrole-2(1H)-carboxylate (13.2 g, 0.04 mol) in toluene (132 mL) was heated at 80° C. for 2 h. Then t-BuOH (66 mL) and PTSA (0.69 g, 0.004 mol) were added to the reaction mixture and allowed to stir at same temperature for 3 h. Progress of reaction was monitored by TLC, which showed consumption of starting material. The reaction mixture was concentrated, diluted with water (250 mL) and extracted with EtOAc (3×150 mL). The organic layer was separated, washed with brine (250 mL), dried ($Na_2SO_4$), filtered and evaporated in vacuum to dryness. The residue was purified by prep HPLC (according to the conditions provided in Table 3) to afford benzyl (3aR,5s,6aS)-5-((tert-butoxycarbonyl) amino-5-methylhexahydro cyclopenta[c]pyrrole-2(1H)-carboxylate (2.5 g) as a white solid and benzyl (3aR,5r,6aS)-5-((tert-butoxycarbonyl)amino)-5-methylhexahydrocyclopenta[c]pyrrole-2(1H)-carboxylate (9.5 g) as a white solid. The stereochemistry of both were determined by 2D-NOESY.

Analytical data of benzyl (3aR,5s, 6aS)-5-((tert-butoxycarbonyl) amino-5-methylhexahydrocyclopenta[c]pyrrole-2 (1H)-carboxylate MS (ESI+ve): 375.16

$^1$H-NMR (400 MHz; DMSO-$d_6$): δ 7.31-7.35 (m, 5H), 6.57 (bs, 1H), 5.05 (s, 2H), 3.35-3.38 (m, 2H), 3.18-3.22 (m,

2H), 2.64-2.69 (m, 2H), 2.33-2.36 (m, 2H), 1.36 (s, 9H), 1.28 (s, 3H), 1.14-1.18 (m, 2H).

Analytical data of benzyl (3aR,5r,6aS)-5-((tert-butoxycarbonyl)amino)-5-methylhexahydro cyclopenta[c]pyrrole-2(1H)-carboxylate MS (ESI+ve): 375.19

$^1$H-NMR (400 MHz; DMSO-$d_6$): δ 7.31-7.35 (m, 5H), 6.78 (bs, 1H), 5.05 (s, 2H), 3.39-3.43 (m, 2H), 3.28-3.32 (m, 2H), 2.60-2.63 (m, 2H), 1.84-1.88 (m, 2H), 1.73-1.77 (m, 2H), 1.36 (s, 9H), 1.19 (s, 3H).

Step 14: Synthesis of tert-butyl ((3aR,5s, 6aS)-5-methyloctahydrocyclopenta[c]pyrrol-5-yl)carbamate (Intermediate A)

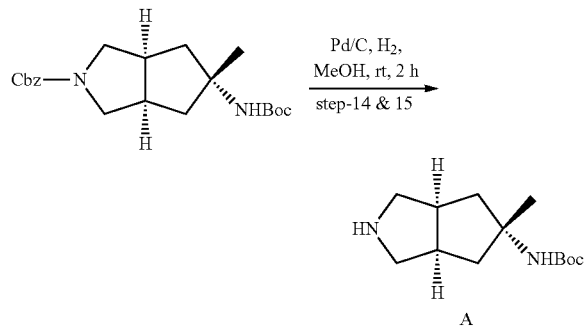

To a stirred solution of benzyl (3aR,5s,6aS)-5-((tert-butoxycarbonyl)amino)-5-methylhexahydrocyclopenta [c]pyrrole-2(1H)-carboxylate (2.5 g, 0.006 mol) in MeOH (25 mL) was added Pd/C (0.73 g, 30% w/w) under N2 atm. The reaction mixture was stirred at rt under H$_2$ atm for 2 h. Progress of reaction was monitored by TLC, which showed consumption of starting material. The reaction mixture was filtered through celite bed and washed with MeOH (80 mL). The filtrate was evaporated under vacuum to afford tert-butyl ((3aR,5s,6aS)-5-methyloctahydrocyclopenta[c]pyrrol-5-yl)carbamate (Intermediate A, 1.36 g, 85%) as an off white solid.

MS (ESI+ve): 241.0

$^1$H-NMR (400 MHz; CD$_3$OD): δ 2.69-2.74 (m, 6H), 2.31-2.36 (m, 2H), 1.42 (s, 9H), 1.36 (s, 3H), 1.10-1.15 (m, 2H).

$^{13}$C-NMR (400 MHz; DMSO d$_6$): 154.4, 76.9, 62.5, 53.5, 45.0, 42.7, 28.3, 23.8

Step 15: Synthesis of tert-butyl ((3aR,5r,6aS)-5-methyloctahydrocyclopenta[c]pyrrol-5-yl)carbamate (compound-A)

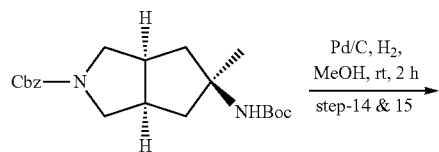

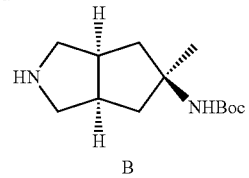

To a stirred solution of benzyl (3aR,5r,6aS)-5-((tert-butoxycarbonyl)amino)-5-methylhexahydrocyclopenta [c]pyrrole-2(1H)-carboxylate (8.2 g, 0.02 mol) in MeOH (82 mL) was added Pd/C (2.4 g, 30% w/w) under N$_2$ atm. The reaction mixture was stirred at rt under H$_2$ atm for 2 h. Progress of reaction was monitored by TLC, which showed consumption of starting material. The reaction mixture was filtered through celite bed and washed with MeOH (250 mL). The filtrate was evaporated under vacuum to dryness. The residue was triturated with diethyl ether and pentane to afford tert-butyl ((3aR,5r,6aS)-5-methyloctahydrocyclopenta[c]pyrrol-5-yl)carbamate (Intermediate B, 5.06 g, 96%) as an off white solid.

MS (ESI+ve): 241.0

$^1$H-NMR (400 MHz; CD$_3$OD): δ 2.79-2.82 (m, 2H), 2.69-2.74 (m, 2H), 2.63-2.65 (m, 2H), 2.02-2.07 (m, 2H), 1.54-1.58 (m, 2H), 1.42 (s, 9H), 1.27 (s, 3H).

$^{13}$C-NMR (400 MHz; DMSO d$_6$): 154.4, 76.9, 59.9, 53.3, 44.8, 41.6, 28.3, 24.5

Example 1: Synthesis of (3aR,5r,6aS)-2-(6-amino-5-(2-chloro-3-methylphenyl)pyrazin-2-yl)-5-methyloctahydrocyclopenta[c]pyrrol-5-amine hydrochloride salt

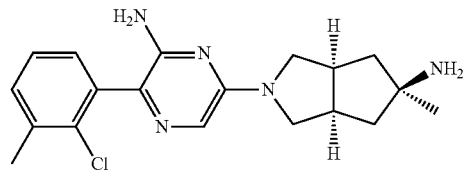 [SMILES: C[C@]1(N)C[C@H]2CN(c3cnc(-c4cccnc4Cl)c(N)n3)C[C@H]2C1]

Step 1: Synthesis of 2-(2-chloro-3-methylphenyl)-4,4,5,5-tetramethyl-1,3,2-dioxaborolane and (2-chloro-3-methylphenyl) boronic acid

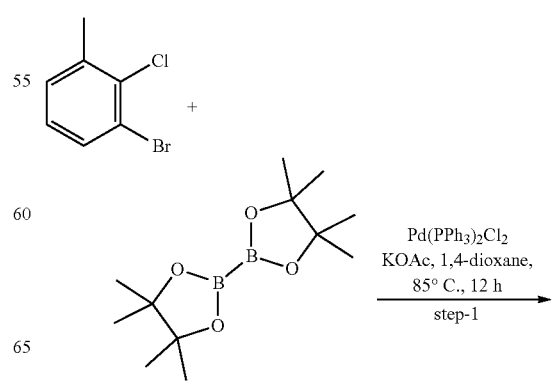

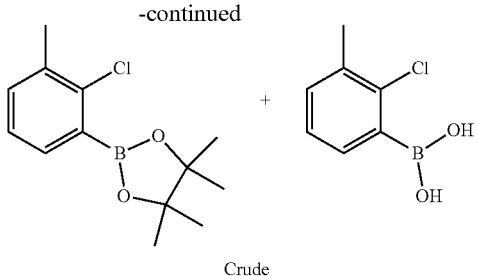

Crude

To a stirred solution of 1-bromo-2-chloro-3-methylbenzene (2 g, 9.73 mmol) in 1,4-dioxane (15 mL), 4,4,4',4',5,5,5',5'-octamethyl-2,2'-bi(1,3,2-dioxaborolane) (3.7 g, 14.6 mmol) and potassium acetate (2.86 g, 29.1 mmol) were added. The reaction mixture was degassed with argon for 10 min. Then Pd(PPh$_3$)$_2$Cl$_2$ (1.02 g, 1.45 mmol) was added and heated at 85° C. with stirring for 12 h. The color of the reaction mixture changed from yellow to red and finally to black. Progress of the reaction was monitored by TLC, which showed consumption of starting material. The reaction mixture was cooled to room temperature and filtered through celite, followed by ethyl acetate wash (100 mL). The filtrate was concentrated to dryness under reduced pressure to afford mixtures of product (1.5 g, 60% pure in LCMS) as a red colored oil, which was used directly for the next step.

Step 2: Synthesis of 6-chloro-3-(2-chloro-3-methylphenyl)pyrazin-2-amine

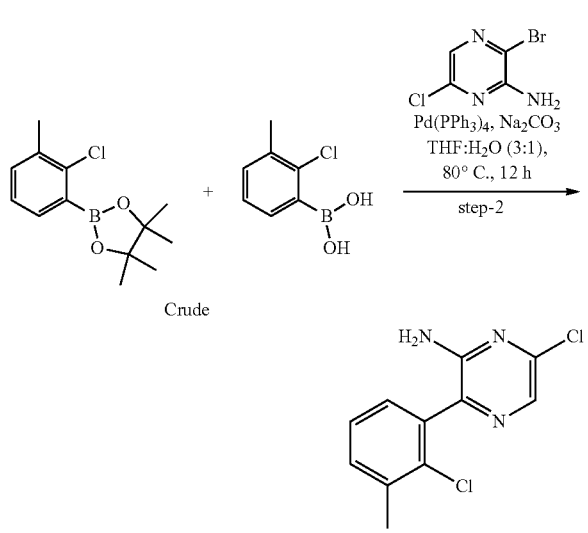

To a stirred solution of 3-bromo-6-chloropyrazin-2-amine (0.3 g, 1.43 mmol) in THF:H$_2$O (20 ml, 9:1), and mixture of boronic acid and ester (0.3 g, crude), sodium carbonate (0.46 g, 4.31 mmol) were added. The reaction mixture was degassed with argon for a 10 minutes and Pd(PPh$_3$)$_4$ (0.16 g, 0.14 mmol) was added. The reaction mixture was degassed again with argon and heated at 80° C. with stirring for 12 h. Progress of the reaction was monitored by TLC, which showed complete consumption of starting material. The reaction mixture was allowed to cool to room temperature and concentrated. The residue was diluted with water (20 mL) and the extracted with EtOAc (3×20 mL). The combined organic layer was washed with brine (40 mL), dried over Na$_2$SO$_4$, filtered, and concentrated. The residue was purified by column chromatography [silica gel (100-200 mesh), gradient 4% to 6% ethyl acetate in hexane] to give 6-chloro-3-(2-chloro-3-methylphenyl)pyrazin-2-amine (0.28 g, 76%) as a yellow solid.

MS (ESI+ve): 253.92

$^1$H-NMR (400 MHz; DMSO-d$_6$): δ 7.82 (s, 1H), 7.44-7.46 (d, J=7.20 Hz, 1H), 7.32-7.36 (t, J=7.6 Hz, 1H), 7.20-7.22 (d, J=6.8 Hz, 1H), 6.51 (bs, 2H), 2.40 (s, 3H).

Step 3: Synthesis of tert-butyl ((3aR,5r,6aS)-2-(6-amino-5-(2-chloro-3-methylphenyl)pyrazin-2-yl)-5-methyloctahydrocyclopenta[c]pyrrol-5-yl)carbamate

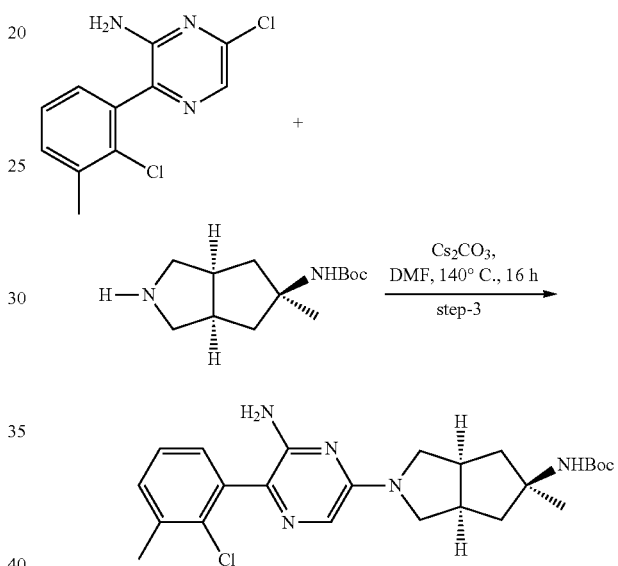

To a stirred solution of 6-chloro-3-(2-chloro-3-methylphenyl)pyrazin-2-amine (0.22 g, 0.92 mmol) in DMF (5 mL), tert-butyl ((3aR,5r,6aS)-5-methyloctahydrocyclopenta[c]pyrrol-5-yl)carbamate (Intermediate B, 0.24 g 0.96 mmol) and cesium carbonate (0.89 g, 2.74 mmol) were added. The reaction mixture was heated at 140° C. for 16 hours. Progress of the reaction was monitored by TLC, which showed consumption of starting material (Note: Boc protecting group was partially removed). The reaction mixture was cooled to room temperature and diluted with water (20 mL) and extracted with ethyl acetate (3×15 mL). The combined organic solution was dried over anhydrous sulfate and concentrated in vacuum to give title compound tert-butyl ((3aR,5r,6aS)-2-(6-amino-5-(2-chloro-3-methylphenyl)pyrazin-2-yl)-5-methyloctahydrocyclopenta[c]pyrrol-5-yl)carbamate (42%) along with (3aR,5r,6aS)-2-(6-amino-5-(2-chloro-3-methylphenyl)pyrazin-2-yl)-5-methyloctahydrocyclopenta[c]pyrrol-5-amine hydrochloride salt (the Compound of Example 1; 16%). The yield of the mixture was 380 mg which was carried forward without further purification.

MS (ESI+ve): 458.12

Step 4: Synthesis of (3aR,5r,6aS)-2-(6-amino-5-(2-chloro-3-methylphenyl)pyrazin-2-yl)-5-methyloctahydrocyclopenta[c]pyrrol-5-amine Hydrochloride salt

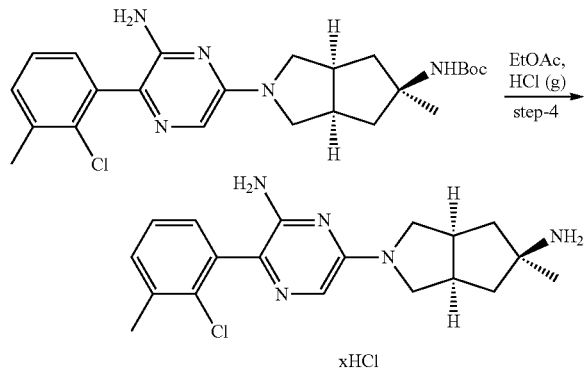

HCl (g) was purged for 20 min over a solution of the crude product mixture from Step 3 (0.37 g) in DCM (15 mL), The reaction mass was monitored by LCMS which showed consumption of the starting material. The volatiles were removed under reduced pressure, triturated with MTBE (20 mL) and the resulting residue was purified by Prep HPLC to afford the title compound (57 mg) (Prep HPLC method mentioned in Table 3).

MS (ESI+ve): 358.27

$^1$H-NMR (400 MHz; CD$_3$OD): δ 7.43-7.45 (d, J=8 Hz, 1H), 7.33-7.37 (t, J=7.56 Hz, 1H), 7.24-7.26 (m, 1H), 7.24 (s, 1H), 3.55-3.59 (m, 4H), 3.03-3.04 (m, 2H), 2.45 (s, 3H), 2.19-2.24 (m, 2H), 1.74-1.79 (m, 2H), 1.42 (s, 3H).

The compounds of Examples 2-6 were prepared in similar manner as Example 1 from Intermediate B. The compounds of Examples 7 and 8 were prepared in similar manner as Example 1 only Intermediate A was used as the starting amine. Spectral data for Examples 2-8 are presented in Table 1.

TABLE 1

| Example No. | Structure | Spectral data |
|---|---|---|
| 2* | (structure shown) | $^1$H-NMR (400 MHz; CD$_3$OD): δ 7.75-7.78 (dd, J = 2.16 Hz, 7.28 Hz, 1H), 7.47-7.50 (m, 2H), 7.30 (s, 1H), 3.66-3.74 (m, 4H), 3.05-3.13 (m, 2H), 2.20-2.25 (m, 2H), 1.79-1.84 (m, 2H), 1.42 (s, 3H). MS (ESI + ve): 378.23 |
| 3 | (structure shown) | $^1$H-NMR (400 MHz; CD$_3$OD): δ 7.46-7.53 (m, 2H), 7.34-7.35 (d, J = 7.20 Hz, 1H), 7.30 (s, 1H), 3.65-3.69 (m, 4H), 3.04-3.06 (m, 2H), 2.20-2.25 (m, 2H), 1.77-1.82 (m, 2H), 1.44 (s, 3H). MS (ESI + ve): 362.21 |
| 4 | (structure shown) | $^1$H-NMR (400 MHz; CD$_3$OD): δ 8.40-8.42(dd, J = 1.76 Hz, 4.84 Hz, 1H), 7.83-7.85 (dd, J = 1.6 Hz, 7.56 Hz, 1H), 7.47-7.50(m, 1H), 7.27 (s, 1H), 3.48-3.58 (m, 4H), 2.98-3.00 (m, 2H), 2.16-2.21 (m, 2H), 1.70-1.75 (m, 2H), 1.39 (s, 3H). MS (ESI + ve): 345.16 |
| 5 | (structure shown) | $^1$H-NMR (400 MHz; CD$_3$OD): δ 7.63-7.67 (m, 1H), 7.43-7.47 (m, 1H), 7.34-7.36 (m, 1H), 7.32 (s, 1H), 3.62-3.69 (m, 4H), 3.04-3.06 (m, 2H), 2.20-2.25 (m, 2H), 1.76-1.80 (m, 2H), 1.43 (s, 3H). MS (ESI + ve): 362.21 |
| 6 | (structure shown) | $^1$H-NMR (400 MHz; CD$_3$OD): δ 7.91-7.93 (m, 1H), 7.71-7.77 (m, 1H), 7.64-7.65 (m, 1H), 7.30 (s, 1H), 3.62-3.64 (m, 4H), 2.98-3.00 (m, 2H), 2.20-2.25 (m, 2H), 1.76-1.81 (m, 2H), 1.43 (s, 3H). MS (ESI + ve): 412.24 |

TABLE 1-continued

| Example No. | Structure | Spectral data |
|---|---|---|
| 7 | 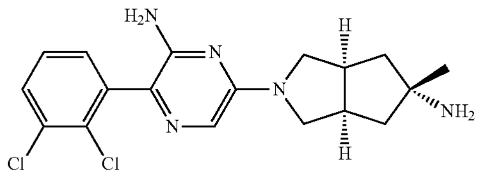 [SMILES: C[C@@]1(N)C[C@H]2CN(c3cnc(-c4cccc(Cl)c4Cl)c(N)n3)C[C@H]2C1] | ¹H-NMR (400 MHz; CDCl₃): δ 7.43-7.48 (m, 1H), 7.38 (s, 1H), 7.20-7.35 (m, 2H), 4.22 (bs, 2H), 3.45-3.60 (m, 2H), 3.38-3.45 (m, 2H), 3.05 (m, 2H), 1.80-2.10 (m, 4H), 1.50-1.60 (m, 2H), 1.30 (s, 3H). MS (ESI + ve): 378.00 |
| 8 | 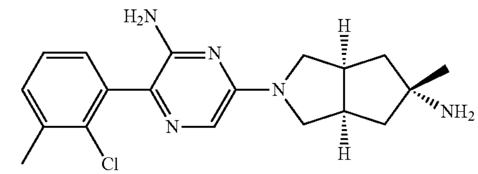 [SMILES: Cc1cccc(-c2ncc(N3C[C@@H]4C[C@@](C)(N)C[C@@H]4C3)nc2N)c1Cl] | ¹H-NMR (400 MHz; CDCl₃): δ 7.40 (s, 1H), 7.18-7.28 (m, 3H), 4.22 (bs, 2H), 3.45-3.60 (m, 2H), 3.38-3.45 (m, 2H), 3.05 (m, 2H), 2.48 (s, 3H), 1.90-2.38 (m, 4H), 1.50-1.60 (m, 2H), 1.30 (s, 3H). MS (ESI + ve): 358.00 |

*This compound was prepared according to the procedures provided in Example 1, using 6-chloro-3-(2,3-dichlorophenyl)pyrazin-2-amine (from Example 9, Step 1) instead of 6-chloro-3-(2-chloro-3-methylphenyl)pyrazin-2-amine in Example 1, Step 3.

Example 9: 6-((3aR,5r,6aS)-5-(aminomethyl)-5-methylhexahydrocyclopenta[c]pyrrol-2(1H)-yl)-3-(2,3-dichlorophenyl)pyrazin-2-amine and 6-((3aR,5s,6aS)-5-(aminomethyl)-5-methylhexahydrocyclopenta[c]pyrrol-2(1H)-yl)-3-(2,3-dichlorophenyl)pyrazin-2-amine

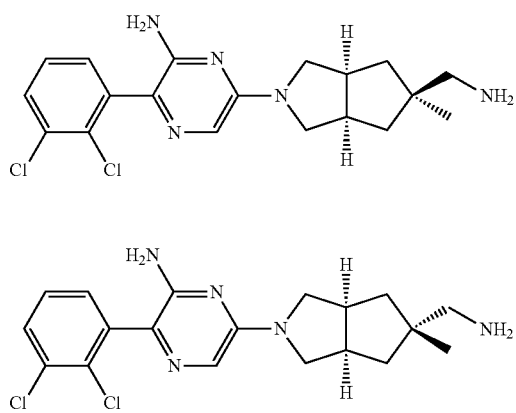

9a

9b

Step 1: Synthesis of 6-chloro-3-(2,3-dichlorophenyl)pyrazin-2-amine

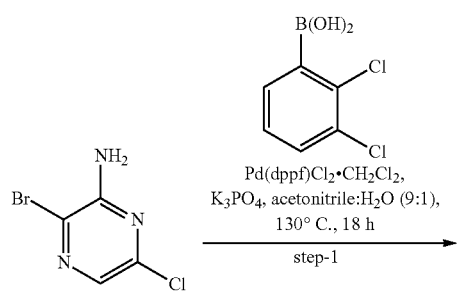

To a stirred solution of 3-bromo-6-chloropyrazin-2-amine (2 g, 9.61 mmol) in ACN: H₂O (20 ml, 9:1), (2,3-dichlorophenyl)boronic acid (2, 2.7 g, 14.2 mmol), potassium phosphate tribasic (6.10 g, 28.8 mmol) were added. The reaction mixture was degassed with argon for a 10 min and Pd(dppf)Cl₂CH₂Cl₂ (0.78 g, 0.96 mmol) was added. The reaction mixture was degassed again with argon and heated at 130° C. with stirring for 18 h. Progress of the reaction was monitored by TLC, which showed complete consumption of starting material. The reaction mixture was allowed to cool to room temperature and concentrated. The residue was diluted with water (100 mL) and the extracted with EtOAc (3×200 mL). The combined organic layer was washed with brine (300 mL), dried over Na₂SO₄, filtered, and concentrated. The residue was purified by column chromatography [silica gel (100-200 mesh), gradient 10-12% ethyl acetate in hexane] to give 6-chloro-3-(2,3-dichlorophenyl)pyrazin-2-amine (1.0 g, 38%) as a yellow solid.

MS (ESI+ve): 274.12

¹H-NMR (400 MHz; CDCl₃): δ 8.02 (s, 1H), 7.58-7.60 (d, J=8.02 Hz, 1H), 7.32-7.36 (m, 2H), 4.63 (bs, 2H).

Step 2: Synthesis of (3aR,6aS)-5-methyloctahydrocyclopenta[c]pyrrole-5-carbonitrile

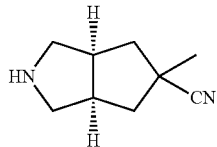

To a stirred solution of benzyl (3aR,6aS)-5-cyano-5-methylhexahydrocyclopenta[c]pyrrole-2(1H)-carboxylate (1 g, 3.51 mol; from the synthesis of Intermediates A and B, Step 8) in EtOH (30 mL) was added Pd/C (0.3 g, 30% w/w) under $N_2$ atm. The reaction mixture was stirred at room temperature under $H_2$ atm for 3 h. Progress of the reaction was monitored by TLC, which showed complete consumption of starting material. The reaction mixture was filtered through a celite bed followed by EtOH wash (80 mL). The filtrate was evaporated under vacuum to dryness. The residue was triturated with diethyl ether to afford (3aR,6aS)-5-methyloctahydrocyclopenta[c]pyrrole-5-carbonitrile (0.5 g, crude) as a sticky brown colored solid diastereomeric mixture (ratio ~3:1 by LCMS) which was used for the next step without further purification MS (ESI+ve): 151.1

Step 3: Synthesis of (3aR,6aS)-2-(6-amino-5-(2,3-dichlorophenyl)pyrazin-2-yl)-5-methyloctahydro cyclopenta[c]pyrrole-5-carbonitrile

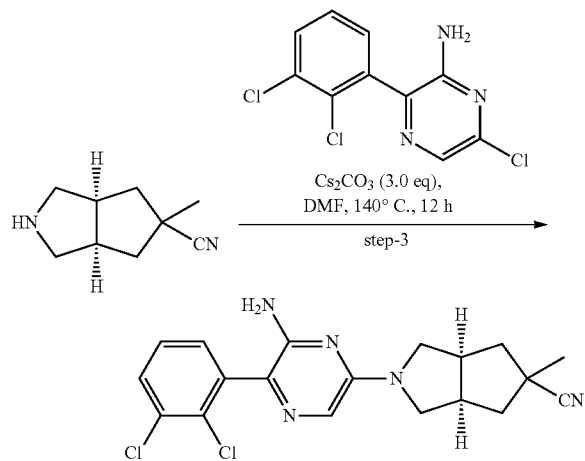

To a stirred solution of (3aR,6aS)-5-methyloctahydrocyclopenta[c]pyrrole-5-carbonitrile (0.32 g, 2.16 mmol) in DMF (8 mL), 6-chloro-3-(2,3-dichlorophenyl)pyrazin-2-amine (0.65 g, 2.38 mmol) and cesium carbonate (2.11 g, 6.49 mmol) were added. The reaction mixture was heated at 140° C. for 12 h. Progress of the reaction was monitored by TLC and crude LCMS, which showed consumption of starting material. The reaction mixture was cooled to room temperature and volatiles were removed under reduced pressure. The resulting material was diluted with water (80 mL) and extracted with ethyl acetate (3×25 mL). The combined organic solution was dried over anhydrous sulfate and concentrated under vacuum. The residue was purified by flash column chromatography using 100-200 mesh silica gel and 10-20% ethyl acetate/hexane as eluent to afford (3aR,6aS)-2-(6-amino-5-(2,3-dichlorophenyl)pyrazin-2-yl)-5-methyloctahydrocyclopenta[c]pyrrole-5-carbonitrile as yellow colored solid diastereomeric mixture (0.26 g, yield: 31%; ratio ~3:1 by $^1$H NMR) which was used for the next step without further diastereomer separation.

MS (ESI+ve): 388.10

$^1$H-NMR (400 MHz; $CD_3OD$): δ 7.58-7.59 (d, J=4 Hz, 1H), 7.30-7.48 (m, 1H), 7.34-7.36 (m, 1H), 7.22 (s, 1H), 3.58-3.60 (m, 4H), 3.10-3.13 (m, 2H), 2.30-2.32 (m, 2H), 1.50-1.52 (m, 2H), 1.49 (s, 1H), 1.43 (s, 3H).

Step 4: Synthesis of 6-((3aR,6aS)-5-(aminomethyl)-5-methylhexahydrocyclopenta[c]pyrrol-2(1H)-yl)-3-(2,3-dichlorophenyl)pyrazin-2-amine

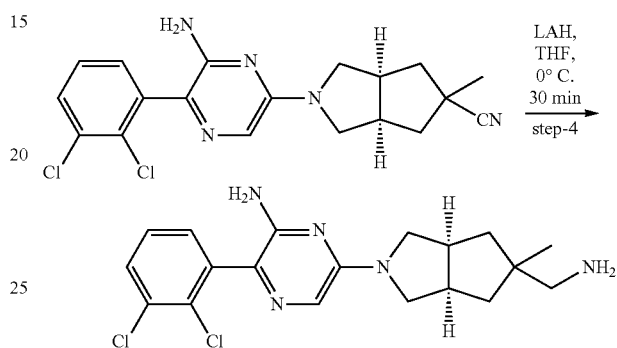

To a stirred solution of LAH (48 mg, 1.23 mmol) in THF (5 mL) at 0° C., a solution of (3aR,6aS)-2-(6-amino-5-(2,3-dichlorophenyl)pyrazin-2-yl)-5-methyloctahydrocyclopenta[c]pyrrole-5-carbonitrile (5, 0.24 g, 0.61 mmol) in THF (5 mL) was added drop wise. The reaction mixture was allowed to stir at rt for 1 h. After consumption of SMs as observed by TLC, the reaction mixture was cooled to 0° C. and quenched with THF: water (9 mL, 9:1) followed by 15% aq. NaOH solution (2 mL) and water (3 mL) over 30 min. The rate of quenching was done carefully so as to maintain the internal temperature below 20° C. The resulting mixture was stirred at rt for 1 h and filtered through celite bed followed by DCM:EtOH (40 mL, 1:1) wash. The collected filtrate was concentrated under reduced pressure to afford (3aR,6aS)-2-(6-amino-5-(2,3-dichlorophenyl)pyrazin-2-yl)-5-methyloctahydrocyclopenta[c]pyrrole-5-carbonitrile (6, crude 220 mg) as brown colored solid with ~2:1 diastereomeric ratio which was purified through SFC using Lux Amylose column, Mobile phase $CO_2$/0.2% DEA in EtOH (60:40) and reverse phase to afford compound 9a as TFA salt (Major, 20 mg, 98% by LCMS) and compound 9b as TFA salt (Minor, 12 mg, 91% by LCMS). The reverse phase purification details are captured in Table 3.

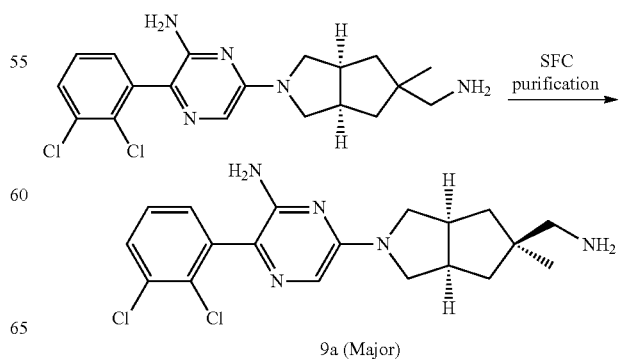

9a (Major)

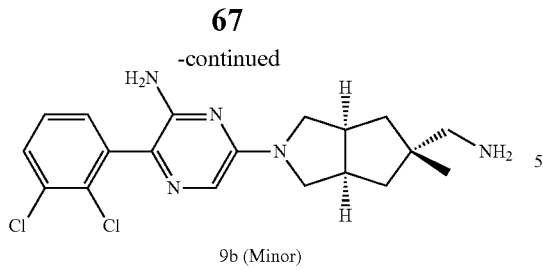

9b (Minor)

6-((3aR,5r,6aS)-5-(aminomethyl)-5-methylhexahydrocyclopenta[c]pyrrol-2(1H)-yl)-3-(2,3-dichlorophenyl)pyrazin-2-amine (9a)

MS (ESI+ve): 392.26

¹H NMR (400 MHz, CD₃OD) δ 7.62-7.65 (dd, J=1.24 Hz, 7.92 Hz, 1H), 7.40-7.43 (t, J=7.76 Hz, 1H), 7.35-7.37 (dd, J=1.32 Hz, 7.72 Hz, 1H), 7.22 (s, 1H), 3.58-3.60 (m, 2H), 3.49-3.51 (m, 2H), 3.04-3.06 (m, 2H), 2.96 (s, 2H), 1.90-1.95 (m, 2H), 1.44-1.49 (m, 2H), 1.15 (s, 3H).

6-((3aR,5s,6aS)-5-(aminomethyl)-5-methylhexahydrocyclopenta[c]pyrrol-2(H)-yl)-3-(2,3-dichlorophenyl)pyrazin-2-amine (9b)

MS (ESI+ve): 392.13

¹H NMR (400 MHz, CD₃OD) δ 7.63-7.65 (dd, J=1.32 Hz, 6.42 Hz, 1H), 7.36-7.40 (m, 2H), 7.22 (s, 1H), 3.56-3.60 (m, 2H), 3.49-3.51 (m, 2H), 2.94-2.96 (m, 2H), 2.89 (s, 2H), 2.02-2.07 (m, 2H), 1.46-1.51 (m, 2H), 1.22 (s, 3H).

Example 10: Synthesis of (3aR,5r,6aS)-2-(4-amino-5-(2-chloro-3-methylphenyl)pyrimidin-2-yl)-5-methyloctahydrocyclopenta[c]pyrrol-5-amine hydrochloride salt

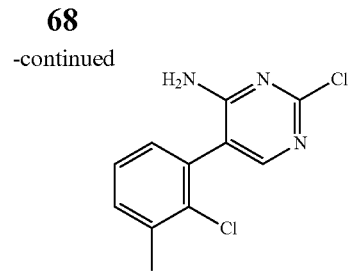

Step 1: Synthesis of 2-chloro-5-(2-chloro-3-methylphenyl)pyrimidin-4-amine

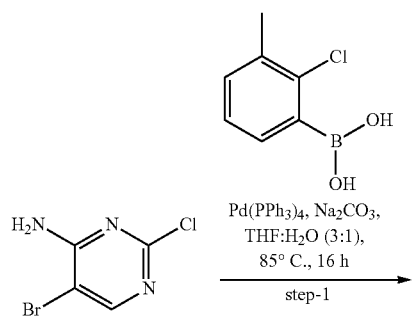

To a stirred solution of 5-bromo-2-chloropyrimidin-4-amine (0.5 g, 2.39 mmol) in THF:H₂O (15 ml, 9:1), 2-chloro-3-methylphenyl)boronic acid (2, 0.61 g, 3.58 mol), sodium carbonate (0.71 g, 7.17 mmol) were added. The reaction mixture was degassed with argon for 10 min and Pd(PPh₃)₄ (0.27 g, 0.24 mmol) was added. The reaction mixture was degassed again with argon and heated at 85° C. with stirring for 16 h. Progress of the reaction was monitored by TLC, which showed consumption of starting material. The reaction mixture was allowed to cool to room temperature and concentrated. The residue was diluted with water (20 mL) and extracted with EtOAc (3×20 mL). The combined organic layer was washed with brine (40 mL), dried over Na₂SO₄, filtered, and concentrated. The residue was purified by column chromatography [silica gel (100-200 mesh), gradient 6-8% ethyl acetate in hexane] to give 2-chloro-5-(2-chloro-3-methylphenyl)pyrimidin-4-amine (0.4 g, 67%) as a pale yellow solid.

MS (ESI+ve): 254.14

¹H-NMR (400 MHz; DMSO-d₆): δ 7.82 (s, 1H), 7.44-7.46 (d, J=7.20 Hz, 1H), 7.32-7.36 (t, J=7.6 Hz, 1H), 7.18-7.20 (d, J=6.8 Hz, 1H), 2.40 (s, 3H).

Step 2: Synthesis of tert-butyl ((3aR,5r,6aS)-2-(4-amino-5-(2-chloro-3-methylphenyl)pyrimidin-2-yl)-5-methyloctahydrocyclopenta[c]pyrrol-5-yl)carbamate

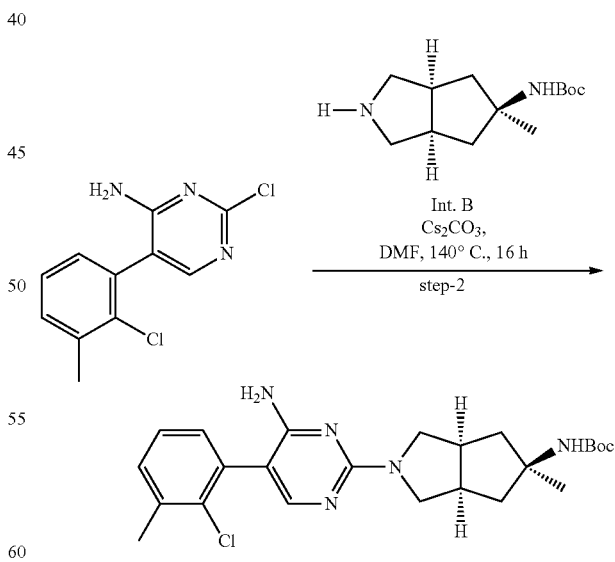

To a stirred solution of 2-chloro-5-(2-chloro-3-methylphenyl)pyrimidin-4-amine (0.22 g, 0.91 mmol) in DMF (5 mL), tert-butyl ((3aR,5r,6aS)-5-methyloctahydrocyclopenta[c]pyrrol-5-yl)carbamate (Intermediate B, 0.24 g 0.96 mmol) and cesium carbonate (0.89 g, 2.74 mmol) were added. The reaction mixture was heated at 140° C. for 16 h.

Progress of the reaction was monitored by TLC, which showed consumption of starting material (Note: Boc protecting group was partially removed) The reaction mixture was cooled to room temperature and diluted with water (20 mL) and extracted with ethyl acetate (3×20 mL). The combined organic solution was dried over anhydrous sulfate and concentrated in vacuum to give 13% of (3aR,5r,6aS)-2-(4-amino-5-(2-chloro-3-methylphenyl)pyrimidin-2-yl)-5-methyloctahydrocyclopenta[c]pyrrol-5-amine along with 23% of (3aR,5r,6aS)-2-(4-amino-5-(2-chloro-3-methylphenyl)pyrimidin-2-yl)-5-methyloctahydrocyclopenta[c]pyrrol-5-amine (the Example compound, 348 mg crude LCMS) which was carried to next step without purification.

Step 3: Synthesis of (3aR,5r,6aS)-2-(4-amino-5-(2-chloro-3-methylphenyl)pyrimidin-2-yl)-5-methyloctahydrocyclopenta[c]pyrrol-5-amine hydrochloride salt

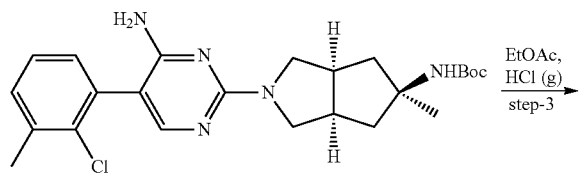

To a stirred solution of the curde products from step 2 (0.34 g) in DCM (25 mL) at 0° C. and HCl gas was purged for 20 min. The resulting mixture was allowed to room temperature and the volatiles were removed under reduced pressure followed by trituration with MTBE (20 mL). The residue so obtained was purified by prep HPLC to afford (3aR,5r,6aS)-2-(4-amino-5-(2-chloro-3-methylphenyl)pyrimidin-2-yl)-5-methyloctahydrocyclopenta[c]pyrrol-5-amine.HCl salt as a yellow solid (15 mg). Prep HPLC method mentioned in Table 3.

MS (ESI+ve): 358.21

$^1$H-NMR (400 MHz; DMSO-d$_6$): δ $^1$H-NMR (400 MHz; CD$_3$OD): δ 7.59 (s, 1H), 7.32-7.34 (d, J=8.00 Hz, 1H), 7.25-7.28 (t, J=7.60 Hz, 1H), 7.12-7.14 (d, J=7.60 Hz, 1H), 3.55-3.64 (m, 4H), 2.93-2.95 (m, 2H), 2.43 (s, 3H), 2.14-2.19 (m, 2H), 1.69-1.74 (m, 2H), 1.38 (s, 3H).

Compounds of Examples 11, 12 and 13 were prepared in similar manner as Example 10 and analytical data are presented in Table 2.

TABLE 2

| Example No. | Structure | Spectral data |
|---|---|---|
| 11 | (structure with two Cl substituents on phenyl) | $^1$H-NMR (400 MHz; CD$_3$OD): δ 7.61 (s, 1H), 7.55-7.57 (dd, J = 1.12 Hz, 7.00 Hz, 1H), 7.34-7.37 (t, J = 7.88 Hz, 1H), 7.24-7.26 (dd, J = 1.08 Hz, 7.56 Hz, 1H), 3.56-3.67 (m, 4H), 2.93-2.95 (m, 2H), 2.13-2.18 (m, 2H), 1.69-1.74 (m, 2H), 1.38 (s, 3H). MS (ESI + ve): 378.20 |
| 12 | (structure with F and Cl substituents on phenyl) •xHCl | $^1$H-NMR (400 MHz; CD$_3$OD): δ 7.65 (s, 1H), 7.44-7.49 (m, 1H), 7.37-7.41 (m, 1H), 7.21-7.23 (d, J = 7.72 Hz, 1H), 3.82-3.84 (m, 2H), 3.69-3.66 (m, 2H), 3.08-3.06 (m, 2H), 2.19-2.23 (m, 2H), 1.82-1.87 (m, 2H), 1.44 (s, 3H). MS (ESI + ve): 362.21 |
| 13 | (structure with pyridine ring with Cl) | $^1$H-NMR (400 MHz; CD$_3$OD): δ 8.37-8.38 (d, J = 3.2 Hz, 1H), 7.76-7.78 (dd, J = 1.52 Hz, 7.48 Hz, 1H), 7.65 (s, 1H), 7.44-7.47 dd, J = 4.88 Hz, 7.48 Hz, 1H), 3.57-3.66 (m, 4H), 2.95-2.96 (m, 2H), 2.16-2.21 (m, 2H), 1.71-1.76 (m, 2H), 1.40 (s, 3H). MS (ESI + ve): 345.24 |

Preparatory HPLC purification conditions are provided in Table 3.

TABLE 3

| Prep HPLC purification methods | | | | | |
|---|---|---|---|---|---|
| Example No. | Phase | Column Name | Gradient | Buffer | Wavelength |
| Intermediates A and B (Step 13) | Normal | Phenomenex Lux Cellulose-2 (21 × 250 mm) 5μ | A:B :: 90:10 Isocratic Run Time: 22 min Flowrate: 20 ml/min | A - n-Hexane B - EtOH | 210 nm |

TABLE 3-continued

Prep HPLC purification methods

| Example No. | Phase | Column Name | Gradient | Buffer | Wavelength |
|---|---|---|---|---|---|
| 11 | Reverse | X Bridge C18 (19 × 250 mm) 10u | (B) 10-48% ACN in 11 mins | (A-) 5 mM Ammonium Acetate. (B-)100% ACN | 214 nm |
| 13 | Reverse | X-Select Hexyl Phenyl(19-250 mm) 5u | (B) 5-30% ACN in 14 mins | (A-) 5 mM Ammonium Acetate. (B)-100% ACN | 214 nm |
| 4 | Reverse | Xtimate Hexyl Phenyl(19 × 250 mm) 10u | (B) 5-35% ACN in 15 mins | (A)-5 mM Ammonium Acetate. (B)-100% ACN | 214 nm |
| 1 | Reverse | Sunfire C18 (19 × 250 mm) 10u | (B) 10-35% ACN in 11 mins | (A)-0.1% TFA in Water (B)-100% ACN | 214 nm |
| 10 | Reverse | X Bridge C18 (19 × 250 mm) 10u | (B) 25-52% ACN in 13 mins. | (A)-5 mM Ammonium Acetate. (B)-100% ACN | 214 nm |
| 9a | Reverse | Sunfire C18 (19 × 250 mm) 10u | (B) 20-50% ACN in 10 mins. | (A)-0.1% TFA in Water (B)-100% ACN | 214 nm |
| 9b | Reverse | Sunfire C18 (19 × 250 mm) 10u | (B) 20-50% ACN in 10 mins. | (A)-0.1% TFA in Water (B)-100% ACN | 214 nm |

Compounds of the invention are assessed for their ability to selectively inhibit SHP2 activity. The inhibitory properties of the compounds of the invention described herein can be evidenced by testing in any one of the following assays.

Example A: SHP2 Inhibition Assay

SHP2 is allosterically activated through binding of bis-tyrosyl-phorphorylated peptides to its Src Homology 2 (SH2) domains. The latter activation step leads to the release of the autoinhibitory interface of SHP2, which in turn renders the SHP2 PTP active and available for substrate recognition and reaction catalysis. The catalytic activity of SHP2 is monitored using the surrogate substrate DiFMUP in a prompt fluorescence assay format. More specifically, the phosphatase reactions are performed at room temperature in a 384-well black polystyrene plate, flat bottom, low flange, nonbinding surface (Corning, cat. no. 3575) using a final reaction volume of 25 µL and the following assay buffer conditions: 60 mM HEPES, pH 7.2, 75 mM NaCl, 75 mM KCl, 1 mM EDTA, 0.05% P-20, 5 mM DTT. The inhibition of SHP2 from the tested compounds (concentrations varying from 0.003 to 100 µM) is monitored using an assay in which 0.5 nM of SHP2 is incubated with of 0.5 µM of peptide IRS1_pY1172(dPEG8)pY1222 (sequence H2N-LN(pY)IDLDLV-(dPEG8)LST(pY) ASINFQK-amide) (SEQ. ID NO 1). After 30-60 min incubation at 25° C., the surrogate substrate DiFMUP (Invitrogen, cat. no. D6567, 200 µM) is added to the reaction and incubated at 25° C. for 30 min (200 µM for residue 2-593, 100 µM for residue 1-525 construct).

The reaction is then quenched by the addition of 5 µL of a 160 µM solution of bpV(Phen) (Enzo Life Sciences cat. no. ALX-270-204). The fluorescence signal is monitored using a microplate reader 2101 multilabel reader (PerkinElmer Envision). The percentage of inhibition is normalized by the total ERK signal and compared with the DMSO vehicle control.

Example B: SHP2 Allosteric Inhibition Assay

SHP2 is allosterically activated through binding of bis-tyrosyl-phorphorylated peptides to its Src Homology 2 (SH2) domains. The latter activation step leads to the release of the autoinhibitory interface of SHP2, which in turn renders the SHP2 protein tyrosine phosphatase (PTP) active and available for substrate recognition and reaction catalysis. The catalytic activity of SHP2 is monitored using the surrogate substrate DiFMUP in a prompt fluorescence assay format.

More specifically, the phosphatase reactions are performed at room temperature in a 384-well black polystyrene plate, flat bottom, low flange, non-binding surface (Corning, Cat#3575) using a final reaction volume of 25 µL and the following assay buffer conditions: 60 mM HEPES, pH 7.2, 75 mM NaCl, 75 mM KCl, 1 mM EDTA, 0.05% P-20, 5 mM DTT.

The inhibition of SHP2 by compounds of the invention (concentrations varying from 0.003-100 µM) are monitored using an assay in which 0.5 nM of SHP2 is incubated with of 0.5 µM of peptide IRS_pY1172(dPEG8)pY1222 (sequence: H2N-LN(pY)IDLDLV(dPEG8)LST(pY)ASIN-FQK-amide) (SEQ ID NO 1). See for instance U.S. Patent Publication 2017/204080 SEQ ID NO:1. After 30-60 minutes incubation at 25° C., the surrogate substrate DiFMUP (Invitrogen, cat# D6567) are added to the reaction and incubated at 25° C. for 30 minutes. The reaction is then quenched by the addition of 5 μl of a 160 μM solution of bpV(Phen) (Enzo Life Sciences cat# ALX-270-204). The fluorescence signal is monitored using a microplate reader (Envision, Perki-Elmer) using excitation and emission wavelengths of 340 nm and 450 nm, respectively. The inhibitor dose response curves may be analyzed using normalized IC50 regression curve fitting with control based normalization.

Example C: p-ERK Cellular Assay p-ERK cellular assay using the AlphaScreen® SureFire™ Phospho-ERK 1/2 Kit (PerkinElmer): KYSE-520 cells (30,000 cells/well) are grown in 96-well plate culture overnight and treated with Shp2 inhibitors at concentrations of 20, 6.6, 2.2, 0.74, 0.24, 0.08, 0.027 μM for 2 hrs at 37° C. Incubations are terminated by addition of 30 μL of lysis buffer (PerkinElmer) supplied with the SureFire phospho-extracellular signal-regulated kinase (pERK) assay kit (PerkinElmer). Samples are processed according to the manufacturer's directions. The fluorescence signal from pERK is measured in duplicate using a 2101 multilabel reader (Perkin Elmer Envision). The percentage of inhibition is normalized by the total ERK signal and compared with the DMSO vehicle control.

Example D: Colony Formation Assay and Cell Proliferation Assay

KYSE-520 Cells (1500 cells/well) are plated onto 24-well plates in 300 μL medium (RPMI-1640 containing 10% FBS, Lonza). For drug treatment, compounds of the invention at various concentrations (20, 10, 5, 2.5, 1.25 μM) are added 24 hours and 5 days after cell plating. At day 11, colonies are stained with 0.2% crystal violet (MP Biomedicals) and subsequently dissolved in 20% acetic acid for quantitation using a Spectramax reader (Thermo Scientific). In cell proliferation assay, cells (1500-cells/well) are plated onto 96-well plates in 100 μL medium (RPMI-1640 containing 10% FBS, Lonza). At day 6, 50 μL Celltiter-Glo reagent (Promega) is added, and the luminescent signal was determined according to the supplier's instruction (Promega).

Example E: Protein Tyrosine Phosphatase (PTP) Assay and $IC_{50}$ Measurements of Inhibitors The phosphatase activity of SHP2 was monitored using the surrogate substrate DiFMUP in a fluorescence assay format. The phosphatase reactions were performed at room temperature in 96-well black polystyrene plate, flat bottom plate using a final reaction volume of 100 μL with the following assay buffer conditions: 60 mM HEPES, pH 7.2, 75 mM NaCl, 75 mM KCl, 1 mM EDTA, 0.05% Tween-20, 5 mM DTT.

To determine the $IC_{50}$ of a compound, an eight-point dose response curve was generated in duplicate. Compounds were incubated at concentrations ranging from 0 μM to 10 μM with 100 ng/mL of human recombinant SHP2 and 0.5 μM of activating peptide IRS1_pY1172(dPEG8)pY1222 (sequence H2N-LN(pY)IDLDLV-(dPEG8)LST(pY)ASIN-FQK-amide) (SEQ ID NO 1). After 30 min incubation at room temperature (23-27° C.), the surrogate substrate DiFMUP (200 μM) was added to the reaction and incubated at room temperature for 30 min. The fluorescence signal was monitored using a microplate reader (Spectramax M5e, Molecular Dynamics) using excitation and emission wavelengths of 340 and 450 nm, respectively. The inhibitor dose-response curves were analyzed using SoftmaxPro v5.2 software.

The compounds of Examples 1, 2, 4, 5, 7, 8, 11, and 12 were found to be SHP2 inhibitors having an $IC_{50}$ less than 9 μM according to the above-described assay. The compound of Example 13 was found to have an $IC_{50}$ of more than 10 μM according to the above-described assay.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety

What is claimed is:
1. A compound of Formula A3a, A3b, or A3c:

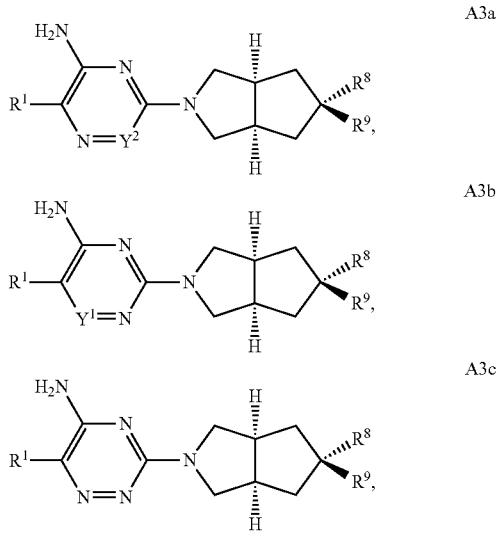

or a pharmaceutically acceptable salt thereof, wherein:
$Y^1$ is N or $CR^{y1}$;
$Y^2$ is N or $CR^{y2}$;
$R^1$ is $C_{6-10}$ aryl, $C_{3-14}$ cycloalkyl, 5-14 membered heteroaryl, or 4-14 membered heterocycloalkyl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(NR^{e1})NR^{c1}R^{d1}$, $NR^{c1}R^{d1}$, $NR^{c1}C(O)R^{b1}$, $NR^{c1}(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, and $C_{2-6}$ alkynyl are optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^8$ and $R^9$ are each independently selected from H, halo, $C_{1-6}$ alkyl, $C_{2-6}$ alkenyl, $C_{2-6}$ alkynyl, $C_{1-4}$ haloalkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)OR^{a2}$ $NR^{c2}C(O)NR^{c2}R^{d2}$ $NR^{c2}S(O)R^{b2}$, $NR^{c2}S(O)_2R^{b2}$ $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the alkyl, $C_{2-6}$ alkenyl, and $C_{2-6}$ alkynyl are optionally substituted with 1, 2, or 3 substituents independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$ $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$ $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

wherein at least one of $R^8$ and $R^9$ is other than H;

$R^{y1}$ and $R^{y2}$ are each independently selected from H, $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$ $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$ $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein the $C_{1-6}$ alkyl, $C_{2-6}$ alkenyl, and $C_{2-6}$ alkynyl are optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$ $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$ $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^2$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})$ $NR^{c3}R^{d3}$ $NR^{c3}R^{d3}$, $NR^{c3}C(O)R^{b3}$, $NR^{c3}C(O)OR^{a3}$, $NR^3C(O)NR^{c3}R^{d3}$ $NR^{c3}$ $S(O)R^{b3}$ $NR^{c3}$ $S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{a1}$, $R^{b1}$, $R^{c1}$, $R^{d1}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_2$-6 alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^{a1}$, $R^{b1}$, Rd, $R^{d1}$, $R^{a3}$, $R^{b3}$, $R^{c3}$, and $R^{d3}$ are each optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)NR^{c7}R^{d4}$, $NR^{c4}C(O)OR^{a4}$, $C(=NR^{e4})NR^{c4}R^{d4}$, $NR^{c4}C(=NR^{e4})NR^{c3}R^{d4}$ $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c1}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c7}R^{d4}$ $NR^{c4}C(O)OR^{a4}$, $C(=NR^{e4})$ $NR^{c4}R^{d4}$, $NR^{c4}C(=NR^{e4})NR^{c3}R^{d4}$, $S(O)R^{b4}$, $S(O)$ $NR^{c4}R^{d4}$, $S(O)_2R^{b4}$, $NR^{c4}S(O)_2R^{b4}$, $NR^{c4}$ $S(O)_2NR^{c4}R^{d4}$, and $S(O)_2NR^{c4}R^{d4}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c7}R^{d4}$ $NR^{c4}C(O)OR^{a4}$, $C(=NR^{e4})$ $NR^{c4}R^{d4}$, $NR^{c4}C(=NR^{e4})NR^{c3}R^{d4}$ $S(O)R^{b4}$, $S(O)$ $NR^{c4}R^{d4}$, $S(O)_2R^{b4}$, $NR^{c4}S(O)_2R^{b4}$, $NR^{c4}$ $S(O)_2NR^{c4}R^{d4}$, and $S(O)_2NR^{c4}R^{d4}$;

each $R^{a2}$, $R^{b2}$, $R^{c2}$, and $R^{d2}$ is independently selected from H and $C_{1-4}$ alkyl;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_2$-6 alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^{e1}$, $R^{e2}$, $R^3$, and $R^{e4}$ is independently selected from H, $C_{1-4}$ alkyl, and CN, wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by an oxo (=O) group.

2. The compound of claim 1, or a pharmaceutically acceptable salt thereof, wherein $Y^1$ is $CR^{Y1}$.

3. The compound of claim 1, or a pharmaceutically acceptable salt thereof, wherein $Y^2$ is $CR^{Y2}$.

4. The compound of claim 1, or a pharmaceutically acceptable salt thereof, wherein $R^1$ is $C_{6-10}$ aryl or 5-14 membered heteroaryl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

5. The compound of claim 1, or a pharmaceutically acceptable salt thereof, wherein $R^1$ is phenyl or 6-membered heteroaryl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

6. The compound of claim 1, or a pharmaceutically acceptable salt thereof, wherein $R^1$ is phenyl or 6-membered heteroaryl, each optionally substituted with 1, 2, 3, 4, or 5 substituents independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

7. The compound of claim 1, or a pharmaceutically acceptable salt thereof, wherein $R^1$ is phenyl or 6-membered heteroaryl, each optionally substituted with 1, 2, 3, 4, or 5 substituents independently selected from halo, $C_{1-6}$ alkyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, $C_{1-6}$ alkyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

8. The compound of claim 1, or a pharmaceutically acceptable salt thereof, wherein $R^1$ is phenyl optionally substituted with 1, 2, or 3 substituents independently selected from F, Cl, methyl, and $CF_3$.

9. The compound of claim 1, or a pharmaceutically acceptable salt thereof, wherein $R^1$ is pyridyl optionally substituted with 1, 2, or 3 substituents independently selected from F, Cl, methyl, and $CF_3$.

10. The compound of claim 1, or a pharmaceutically acceptable salt thereof, wherein $R^8$ and $R^9$ are each independently selected from H, halo, $C_{1-6}$ alkyl, $C_{1-4}$ haloalkyl, $OR^{a2}$, and $NR^{c2}R^{d2}$, wherein the alkyl is optionally substituted with 1, 2, or 3 substituents independently selected from halo, $OR^{a2}$, and $NR^{c2}R^{d2}$.

11. The compound of claim 1, or a pharmaceutically acceptable salt thereof, wherein $R^8$ and $R^9$ are each independently selected from H, $C_{1-4}$ alkyl, OH, and $NH_2$, wherein the alkyl is optionally substituted with $NH_2$.

12. The compound of claim 1, or a pharmaceutically acceptable salt thereof, wherein $R^8$ and $R^9$ are each independently selected from methyl and $NH_2$.

13. The compound of claim 1, or a pharmaceutically acceptable salt thereof, wherein $R^{Y1}$ and $R^{Y2}$ are each independently selected from H, $C_{1-6}$ alkyl, and $NR^{c3}R^{d3}$, wherein the $C_{1-6}$ alkyl is optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

14. The compound of claim 1, or a pharmaceutically acceptable salt thereof, wherein $R^{Y1}$ is H.

15. The compound of claim 1, or a pharmaceutically acceptable salt thereof, wherein $R^{Y2}$ is H.

16. The compound of claim 1 selected from:
(3aR,5r,6aS)-2-(6-amino-5-(2-chloro-3-methylphenyl)pyrazin-2-yl)-5-methyloctahydrocyclopenta[c]pyrrol-5-amine;
(3aR,5r,6aS)-2-(6-amino-5-(2,3-dichlorophenyl)pyrazin-2-yl)-5-methyloctahydrocyclopenta[c]pyrrol-5-amine;
(3aR,5r,6aS)-2-(6-amino-5-(2-chloro-3-fluorophenyl)pyrazin-2-yl)-5-methyloctahydrocyclopenta[c]pyrrol-5-amine;
(3aR,5r,6aS)-2-(6-amino-5-(2-chloropyridin-3-yl)pyrazin-2-yl)-5-methyloctahydrocyclopenta[c]pyrrol-5-amine;
(3aR,5r,6aS)-2-(6-amino-5-(3-chloro-2-fluorophenyl)pyrazin-2-yl)-5-methyloctahydrocyclopenta[c]pyrrol-5-amine;
(3aR,5r,6aS)-2-(6-amino-5-(2-chloro-3-(trifluoromethyl)phenyl)pyrazin-2-yl)-5-methyloctahydrocyclopenta[c]pyrrol-5-amine;
(3aR,5s,6aS)-2-(6-amino-5-(2,3-dichlorophenyl)pyrazin-2-yl)-5-methyloctahydrocyclopenta[c]pyrrol-5-amine;

(3aR,5s,6aS)-2-(6-amino-5-(2-chloro-3-methylphenyl)pyrazin-2-yl)-5-methyloctahydrocyclopenta[c]pyrrol-5-amine;

6-((3 aR, 5r,6aS)-5-(aminomethyl)-5-methylhexahydrocyclopenta[c]pyrrol-2(1H)-yl)-3-(2,3-dichlorophenyl)pyrazin-2-amine;

6-((3aR,5s,6aS)-5-(aminomethyl)-5-methylhexahydrocyclopenta[c]pyrrol-2(1H)-yl)-3-(2,3-dichlorophenyl)pyrazin-2-amine;

(3aR,5r,6aS)-2-(4-amino-5-(2-chloro-3-methylphenyl)pyrimidin-2-yl)-5-methyloctahydrocyclopenta[c]pyrrol-5-amine;

(3 aR, 5r,6aS)-2-(4-amino-5-(2,3-dichlorophenyl)pyrimidin-2-yl)-5-methyloctahydrocyclopenta[c]pyrrol-5-amine;

(3aR,5r,6aS)-2-(4-amino-5-(2-chloro-3-fluorophenyl)pyrimidin-2-yl)-5-methyloctahydrocyclopenta[c]pyrrol-5-amine; and (3aR,5r,6aS)-2-(4-amino-5-(2-chloropyridin-3-yl)pyrimidin-2-yl)-5-methyloctahydrocyclopenta[c]pyrrol-5-amine;

or a pharmaceutically acceptable salt thereof.

17. A pharmaceutical composition comprising a compound of claim 1, or a pharmaceutically acceptable salt thereof, and a pharmaceutically acceptable carrier.

18. The compound of claim 1 having Formula A3a:

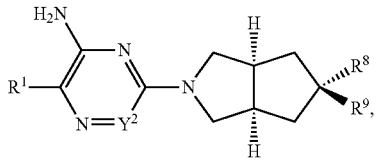

A3a or a pharmaceutically acceptable salt thereof.

19. The compound of claim 1 having Formula A3b:

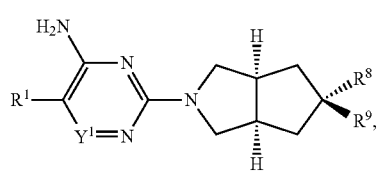

A3b or a pharmaceutically acceptable salt thereof.

20. The compound of claim 1 having Formula A3c:

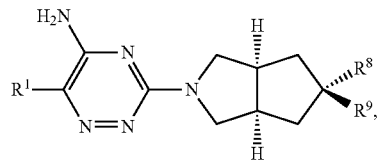

A3c or a pharmaceutically acceptable salt thereof.

* * * * *